US009186177B2

(12) United States Patent
Whitman et al.

(10) Patent No.: US 9,186,177 B2
(45) Date of Patent: *Nov. 17, 2015

(54) TROCAR DEVICE

(75) Inventors: Michael P. Whitman, New Hope, PA (US); John E. Burbank, Ridgefield, CT (US); Jeremy Hill, Middlebury, CT (US); Thomas Guy, Tequesta, FL (US)

(73) Assignee: Covidien LP, Mansfield, MA (US)

( * ) Notice: Subject to any disclaimer, the term of this patent is extended or adjusted under 35 U.S.C. 154(b) by 896 days.

This patent is subject to a terminal disclaimer.

(21) Appl. No.: 13/031,643

(22) Filed: Feb. 22, 2011

(65) Prior Publication Data

US 2011/0166587 A1   Jul. 7, 2011

Related U.S. Application Data

(62) Division of application No. 10/098,217, filed on Mar. 14, 2002, now Pat. No. 7,905,897.

(60) Provisional application No. 60/275,869, filed on Mar. 14, 2001.

(51) Int. Cl.
*A61B 17/32* (2006.01)
*A61B 17/34* (2006.01)

(52) U.S. Cl.
CPC ... *A61B 17/3476* (2013.01); *A61B 2017/32006* (2013.01); *A61B 2017/3409* (2013.01); *A61B 2017/3458* (2013.01)

(58) Field of Classification Search
CPC ............... A61B 17/3476; A61B 2017/32006; A61B 2017/3409; A61B 2017/3458
USPC .......... 606/167–173, 184, 185; 600/566–568; 409/138
See application file for complete search history.

(56) References Cited

U.S. PATENT DOCUMENTS

| 530,791 | A | | 12/1894 | Newton | |
|---|---|---|---|---|---|
| 3,126,889 | A | * | 3/1964 | Blumenfeld | 606/180 |
| 3,193,165 | A | | 7/1965 | Akhalaya et al. | |
| 3,357,422 | A | * | 12/1967 | Creelman | 600/564 |
| 3,388,847 | A | | 6/1968 | Kasulin et al. | |
| 3,945,375 | A | * | 3/1976 | Banko | 600/104 |
| 3,990,453 | A | | 11/1976 | Douvas et al. | |
| 4,060,089 | A | | 11/1977 | Noiles | |
| 4,423,730 | A | | 1/1984 | Gabbay | |
| 4,445,509 | A | | 5/1984 | Auth | |
| 4,461,305 | A | | 7/1984 | Cibley | |
| 4,472,880 | A | | 9/1984 | Johansson | |
| 4,505,414 | A | | 3/1985 | Filipi | |
| 4,535,773 | A | | 8/1985 | Yoon | |

(Continued)

FOREIGN PATENT DOCUMENTS

DE   43 12 147 A1   10/1993
EP   0 653 922 B1   12/1999

*Primary Examiner* — Ryan Severson
*Assistant Examiner* — Rachel S Papeika

(57) ABSTRACT

A surgical device is described. The surgical device may comprise a rotatable cutter configured to cut tissue for insertion of a cannula, and a first driver configured to be driven by a motor arrangement and to rotate the cutter. The surgical device may further include, for example, the cannula, at least one of the rotatable cutter and the first driver being disposed in a bore of the cannula. In one embodiment, the rotatable cutter may include an auger having a cutting thread. In another embodiment, the rotatable cutter may include a disk-shaped blade.

11 Claims, 27 Drawing Sheets

(56) References Cited

U.S. PATENT DOCUMENTS

| | | | |
|---|---|---|---|
| 4,574,806 A | 3/1986 | McCarthy | |
| 286,567 A | 11/1986 | Lichtman et al. | |
| 4,654,030 A | 3/1987 | Moll et al. | |
| 4,682,606 A * | 7/1987 | DeCaprio | 600/567 |
| 4,813,102 A | 3/1989 | Ailey, Jr. | |
| 4,902,280 A | 2/1990 | Lander | |
| 4,936,845 A | 6/1990 | Stevens | |
| 4,940,468 A | 7/1990 | Petillo | |
| 4,998,527 A | 3/1991 | Meyer | |
| 5,012,582 A | 5/1991 | Bristol et al. | |
| 5,030,206 A | 7/1991 | Lander | |
| 5,047,026 A | 9/1991 | Rydell | |
| 5,059,203 A * | 10/1991 | Husted | 606/159 |
| 5,112,272 A | 5/1992 | Anderson | |
| 5,133,359 A | 7/1992 | Kedem | |
| 5,152,744 A | 10/1992 | Krause et al. | |
| 5,156,315 A | 10/1992 | Green et al. | |
| 5,186,714 A | 2/1993 | Boudreault et al. | |
| 5,217,030 A | 6/1993 | Yoon | |
| 5,221,281 A | 6/1993 | Klicek | |
| 5,224,951 A | 7/1993 | Freitas | |
| 5,226,426 A | 7/1993 | Yoon | |
| 5,249,583 A | 10/1993 | Mallaby | |
| 5,256,149 A | 10/1993 | Banik et al. | |
| RE34,556 E | 3/1994 | Sjostrom et al. | |
| 5,324,300 A | 6/1994 | Elias et al. | |
| 5,342,382 A | 8/1994 | Brinkerhoff et al. | |
| 5,344,420 A | 9/1994 | Hilal et al. | |
| 5,346,497 A | 9/1994 | Simon et al. | |
| 5,368,607 A | 11/1994 | Freitas | |
| 5,380,321 A | 1/1995 | Yoon | |
| 5,385,552 A * | 1/1995 | Haber et al. | 604/167.03 |
| 5,391,156 A | 2/1995 | Hildwein et al. | |
| 5,400,267 A | 3/1995 | Denen et al. | |
| 5,423,330 A * | 6/1995 | Lee | 600/566 |
| 5,423,799 A * | 6/1995 | Shiu | 606/159 |
| 5,460,182 A | 10/1995 | Goodman et al. | |
| 5,507,764 A * | 4/1996 | Muller | 606/180 |
| 5,526,822 A | 6/1996 | Burbank et al. | |
| 5,549,565 A | 8/1996 | Ryan et al. | |
| 5,562,677 A | 10/1996 | Hildwein et al. | |
| 5,569,285 A | 10/1996 | Webb | |
| 5,569,289 A | 10/1996 | Yoon | |
| 5,571,133 A | 11/1996 | Yoon | |
| 5,571,134 A | 11/1996 | Yoon | |
| 5,573,545 A | 11/1996 | Yoon | |
| 5,575,804 A | 11/1996 | Yoon | |
| 5,584,848 A | 12/1996 | Yoon | |
| 5,591,186 A | 1/1997 | Wurster et al. | |
| 5,591,191 A * | 1/1997 | Kieturakis | 606/185 |
| 5,591,196 A | 1/1997 | Marin et al. | |
| 5,597,107 A | 1/1997 | Knodel et al. | |
| 5,599,347 A | 2/1997 | Hart et al. | |
| 5,607,440 A | 3/1997 | Danks et al. | |
| 5,632,758 A * | 5/1997 | Sklar | 606/170 |
| 5,643,298 A * | 7/1997 | Nordgren et al. | 606/159 |
| 5,662,673 A | 9/1997 | Kieturakis | |
| 5,662,680 A | 9/1997 | Desai | |
| 5,665,072 A | 9/1997 | Yoon | |
| 5,674,237 A | 10/1997 | Ott | |
| 5,676,681 A | 10/1997 | Yoon | |
| 5,676,682 A | 10/1997 | Yoon | |
| 5,676,683 A | 10/1997 | Yoon | |
| 5,685,820 A | 11/1997 | Riek et al. | |
| 5,688,286 A | 11/1997 | Yoon | |
| 5,693,031 A | 12/1997 | Ryan et al. | |
| 5,713,870 A | 2/1998 | Yoon | |
| 5,730,755 A | 3/1998 | Yoon | |
| 5,795,308 A | 8/1998 | Russin | |
| 5,797,944 A | 8/1998 | Nobles et al. | |
| 5,807,317 A | 9/1998 | Krech, Jr. | |
| 5,807,402 A | 9/1998 | Yoon | |
| 5,830,191 A | 11/1998 | Hildwein et al. | |
| 5,849,023 A | 12/1998 | Mericle | |
| 5,868,711 A | 2/1999 | Kramer et al. | |
| 5,871,471 A | 2/1999 | Ryan et al. | |
| 5,901,424 A | 5/1999 | Rector | |
| 5,906,595 A | 5/1999 | Powell et al. | |
| 5,931,848 A | 8/1999 | Saadat | |
| 5,947,930 A | 9/1999 | Schwemberger et al. | |
| 5,957,947 A | 9/1999 | Wattiez et al. | |
| 5,984,919 A | 11/1999 | Hilal et al. | |
| 5,993,454 A | 11/1999 | Longo | |
| 5,997,510 A | 12/1999 | Schwemberger | |
| 6,033,420 A | 3/2000 | Hahnen | |
| 6,063,099 A | 5/2000 | Danks et al. | |
| 6,106,535 A * | 8/2000 | Dross et al. | 606/171 |
| 6,142,930 A | 11/2000 | Ito et al. | |
| 6,146,400 A | 11/2000 | Hahnen | |
| 6,168,607 B1 | 1/2001 | Wattiez et al. | |
| 6,224,608 B1 | 5/2001 | Ciccolella et al. | |
| 6,261,241 B1 | 7/2001 | Burbank et al. | |
| 6,264,087 B1 | 7/2001 | Whitman | |
| 6,315,184 B1 | 11/2001 | Whitman | |
| 6,346,072 B1 | 2/2002 | Cooper | |
| 6,348,061 B1 | 2/2002 | Whitman | |
| 6,443,973 B1 | 9/2002 | Whitman | |
| 6,488,197 B1 | 12/2002 | Whitman | |
| 6,491,201 B1 | 12/2002 | Whitman | |
| 6,533,157 B1 | 3/2003 | Whitman | |
| 6,758,824 B1 | 7/2004 | Miller et al. | |
| 7,905,897 B2 | 3/2011 | Whitman et al. | |
| 2001/0031975 A1 | 10/2001 | Whitman et al. | |
| 2002/0049454 A1 | 4/2002 | Whitman et al. | |
| 2002/0077645 A1 | 6/2002 | Wiener et al. | |
| 2002/0198554 A1 | 12/2002 | Whitman et al. | |
| 2003/0073981 A1 * | 4/2003 | Whitman et al. | 606/1 |

* cited by examiner

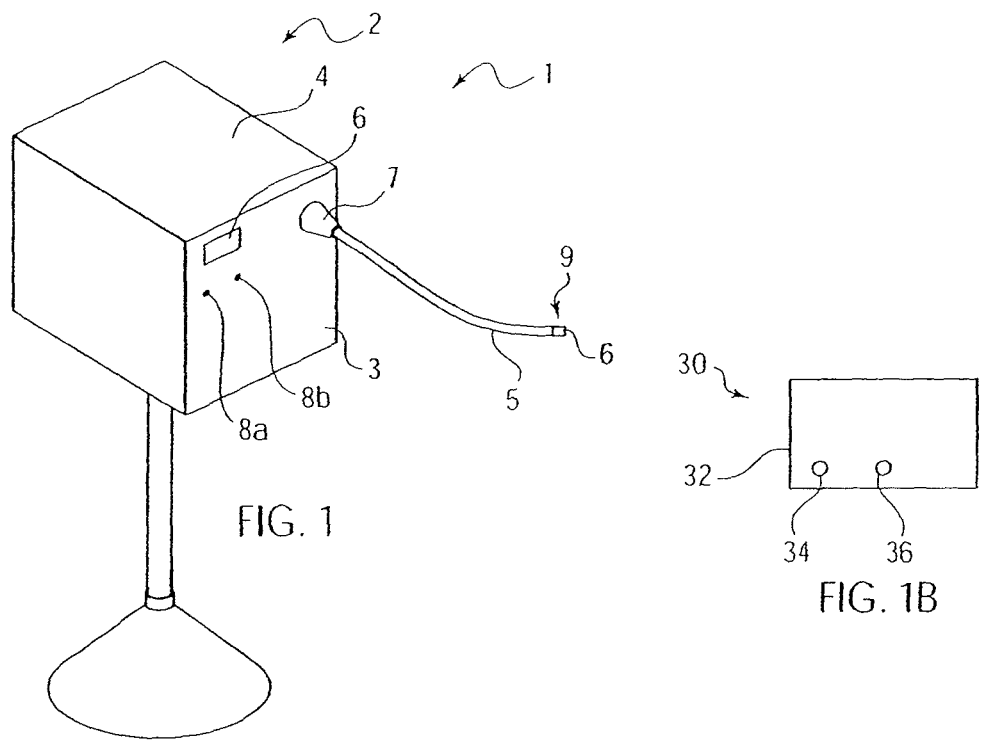
FIG. 1
FIG. 1B
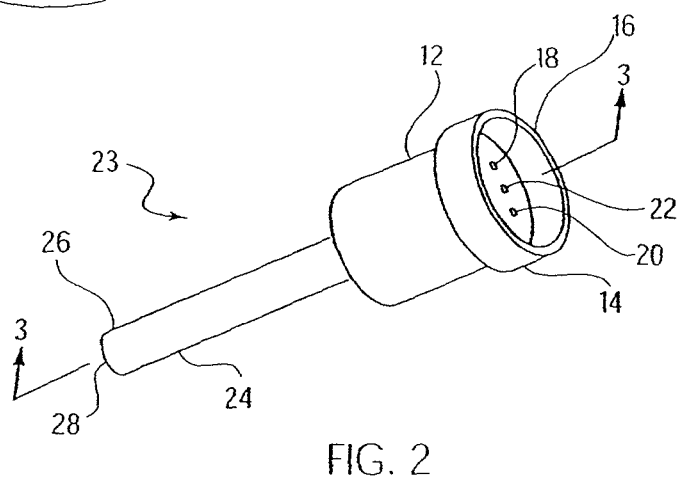
FIG. 2

TROCAR DEVICE

RELATED U.S. APPLICATION DATA

This application is a divisional application which claims the benefit of and priority to U.S. patent application Ser. No. 10/098,217, filed on Mar. 14, 2002, now U.S. Pat. No. 7,905,897, which claims the benefit of and priority to U.S. Provisional Patent Application Ser. No. 60/275,869, filed on Mar. 14, 2001, the entire content of each of which is incorporated herein by reference.

This application relates to U.S. patent application Ser. No. 09/324,452, filed on Jun. 2, 1999, entitled "Electromechanical Driver Device For Use With Anastomosing, Stapling, and Resecting instruments," U.S. patent application Ser. No. 09/510,923, filed on Feb. 22, 2000, entitled "A Carriage Assembly For Controlling a Steering Wire Mechanism Within a Flexible Shaft," U.S. patent application Ser. No. 09/723,715, filed on Nov. 28, 2000, entitled "Electro-Mechanical Surgical Device," U.S. Provisional Patent Application Ser. No. 60/275,869, filed on Mar. 14, 2001, entitled "Trocar Device," U.S. patent Ser. No. 09/887,789, filed on Jun. 22, 2001, entitled "Electro-Mechanical Surgical Device," U.S. patent Ser. No. 09/836,781, filed on Apr. 17, 2001, entitled "Electro-Mechanical Surgical Device", and U.S. Provisional Patent Application No. 60/337,544, filed on Dec. 4, 2001, entitled "Calibration of a Surgical Instrument," each of which is expressly incorporated herein in its entirety by reference.

FIELD OF THE INVENTION

The present invention relates to a trocar device and a cannula.

BACKGROUND OF THE INVENTION

The literature is replete with descriptions of trocar devices, particularly surgical trocar devices. For example, a conventional trocar may include, for example, a seal, a sharp trocar, a cannula, and a safety shield to protect organs once the trocar has penetrated the abdominal wall. The safety shield is generally designed as a mechanical device which is spring-loaded and activated when the trocar tip is inserted into the cannula. The tip of the trocar is protected by the safety shield. As the trocar passes through the layers of the abdominal wall, the safety shield is retracted, exposing the sharp tip of the trocar. When the device finally penetrates the last layer of abdominal tissue, and just prior to entering the open space of the abdomen, the safety shield moves forward to again cover the trocar tip.

The instrument described above suffers numerous disadvantages. For example, if the mechanical safety shield were to become stuck, due to abdominal wall tissue becoming entrapped, the safety shield would not spring forward to cover the sharp trocar. In this case, damage could occur. In fact, damage does occur in a certain number of surgical cases annually. In addition, an unpredictable force is generally required to overcome the resistance of the tissue of the abdominal wall. This force is provided by the user pushing linearly, the trocar handle toward the abdomen. Since the force is variable and unique to the given tissue composition, the user cannot accurately predict how much force may be required on any given insertion.

A further disadvantage of the above-described instruments and systems is the lack of any feedback to the operator as to when then instrument has actually entered into the abdominal cavity. This can lead to damage of vital organs and misuse of the instrument.

A further disadvantage of the above-described instruments and systems is that such instruments and systems typically require manual manipulation and operation. This then requires the user to interpret what constitutes excessive force. When excessive force is used, damage to vital organs can occur.

A further disadvantage of the above-described instruments and systems is that such instruments and systems typically utilize a diamond-pointed-like trocar which penetrates the abdomen like a nail penetrates wood when hammered. This trocar placement method does not account for the potential variation in tissue thickness, tissue variability within the abdominal wall, and does not allow for counter-traction which would provide the users with the need to apply less force.

SUMMARY

An example embodiment of the present invention includes a surgical device comprising a rotatable cutter configured to cut tissue for insertion of a cannula, and a first driver configured to be driven by a motor arrangement and to rotate the cutter. The surgical device may further include, for example, the cannula, at least one of the rotatable cutter and the first driver being disposed in a bore of the cannula. In one embodiment, the rotatable cutter may include an auger having a cutting thread. In another embodiment, the rotatable cutter may include a disk-shaped blade.

BRIEF DESCRIPTION OF THE DRAWINGS

The features and the elements characteristic of the present invention are set forth with particularity in the appended claims. The present invention itself, however, both as to organization and method of operation, may best be understood by reference to the detailed description which follows taken in conjunction with the accompanying drawings in which:

FIG. 1 is a perspective view of an example electro-mechanical driver device, which is coupleable to an example trocar device according to the present invention.

FIG. 1B is a top schematic view of an example remote control unit of the electro-mechanical driver device illustrated in FIG. 1.

FIG. 2 is a perspective view of an example trocar device according to the present invention.

DETAILED DESCRIPTION OF THE INVENTION

Figure 1A:
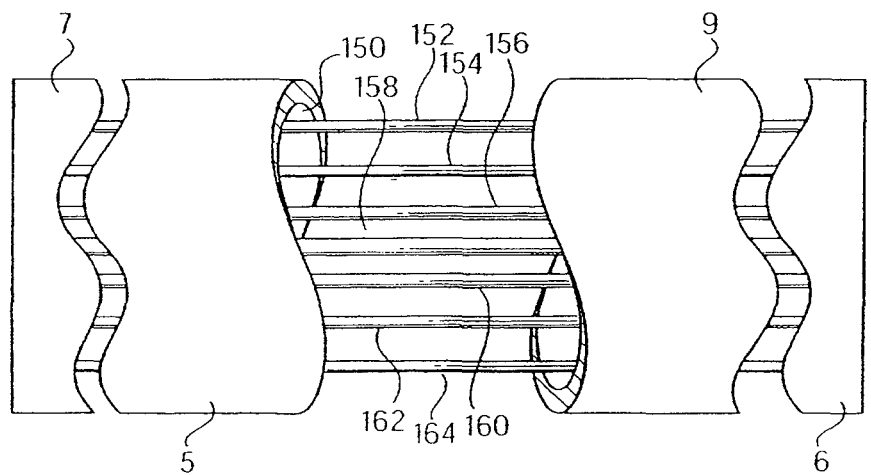
FIG. 1A is a detailed view of the interior of a flexible shaft of the electro-mechanical surgical device illustrated in FIG. 1.

Those skilled in the art will gain an appreciation of the present invention from a reading of the following description when viewed in conjunction with the accompanying drawings of FIGS. 1-14E, inclusive. The individual reference characters designate the same or similar elements throughout the several views.

Referring to FIG. 1, a perspective view of an electro-mechanical driver device 1 according to one embodiment of the present invention is shown. Electro-mechanical driver device 1 may include, for example, a remote power console 2, which includes a housing 4 having a front panel 3. Mounted on front panel 3 are a display device 6 and indicators 8a, 8b. A flexible shaft 5 may extend from housing 4 and may be detachably secured thereto via a first coupling 7. The distal end 9 of flexible shaft 5 may include a second coupling 6 adapted to detachably secure a surgical instrument or attachment to the distal end 9 of flexible shaft 5. The surgical instrument or attachment may be, for example, a trocar device according to the present invention. Other surgical instruments are described, for example, in U.S. patent application Ser. No. 09/324,451, entitled "A Stapling Device for Use with an Electro-mechanical Driver Device for Use with Anastomosing, Stapling, and Resecting Instruments," U.S. patent application Ser. No. 09/324,452, entitled "Electro-mechanical Driver Device for Use with Anastomosing, Stapling, and Resecting Instruments," U.S. patent application Ser. No. 09/351,534, entitled "Automated Surgical Stapling System," U.S. patent application Ser. No. 09/510,926, entitled "A Vessel and Lumen Expander Attachment for Use with an Electro-mechanical Driver Device," U.S. patent application Ser. No. 09/510,927, entitled "Electro-mechanical Driver and Remote Surgical Instruments Attachment Having Computer Assisted Control Capabilities," U.S. patent application Ser. No. 09/510,931, entitled "A Tissue Stapling Attachment for Use with an Electro-mechanical Driver Device," U.S. patent application Ser. No. 09/510,932, entitled "A Fluid Delivery Mechanism for Use with Anastomosing, Stapling, and Resecting Instruments," and U.S. patent application Ser. No. 09/510,933, entitled "A Fluid Delivery Device for Use with Anastomosing, Stapling, and Resecting Instruments," each of which is expressly incorporated herein in its entirety by reference thereto.

According to one embodiment, the flexible shaft 5 includes a tubular outer sheath, which may include a coating or other sealing arrangement to provide a fluid-tight seal between the interior channel thereof and the environment. The sheath may be formed of a tissue-compatible, sterilizable elastomeric material. The sheath may also be formed of a material that is autoclavable. Disposed within the interior channel 150 of the flexible shaft 5, and extending along the entire length thereof, as shown in FIG. 1A, may be a first rotatable drive shaft 152, a second rotatable drive shaft 154, a first steering cable 156, a second steering cable 158, a third steering cable 160, a fourth steering cable 162 and/or a data transfer cable 164, all terminating at the second coupling 6, at the distal end 9 of the flexible shaft 5. It will be appreciated by those skilled in the art that the combined functions of the electro-mechanical driver and control units is to provide force and control data, and that one function of the flexible shaft is to communicate that force and control data from the trocar device of the present invention.

The remote power console 2 may include a motor system, which includes one or more motors configured to rotate the first and second rotatable drive shafts and to apply tension or otherwise drive the steering cables to thereby steer the distal end 9 of the flexible shaft 5.

Referring now to FIG. 1B, there is seen a top schematic view of a remote control unit ("RCU") 30 of the electro-mechanical driver device 1 illustrated in FIG. 1. The RCU 30 may be, for example, a wired remote control unit, a wireless remote control unit, a hybrid remote control unit, etc. The RCU 30 may include a number of operable control elements 34, 36, which may be, for example, toggle switches, button switches, analog switches, control knobs, potentiometers, etc. It should be understood that although FIG. 1B illustrates two control elements 34, 36, any appropriate number of control elements may be provided.

Referring now to FIG. 2, there is seen a perspective view of a first exemplary embodiment of a trocar device 23 according to the present invention. Trocar device 23 may be used in combination with an electro-mechanical driver device, such as that described in U.S. patent application Ser. No. 09/324,452, entitled "Electro-mechanical Driver Device for Use with Anastomosing, Stapling, and Resecting Instruments," U.S. patent application Ser. No. 09/510,927, entitled "Electro-mechanical Driver and Remote Surgical Instruments Attachment Having Computer Assisted Control Capabilities," U.S. patent application Ser. No. 09/723,715, entitled "Electro-Mechanical Surgical Device," U.S. patent application Ser. No. 09/836,781, entitled "Electro-Mechanical Surgical Device", and U.S. patent application Ser. No. 09/887,789, entitled "Electro-Mechanical Surgical Device," each of which is expressly incorporated herein in its entirety by reference thereto. Trocar device 23 may also be used in combination with a manually-operable driver device.

Trocar device 23 includes a housing 12, which includes a coupling 14 adapted and configured to detachably couple the trocar device 23 with the second coupling 6 of the flexible shaft 5 of the driver device. The couplings 6 and 14 may be a quick-connect type fitting, such as a rotary quick-connect type fitting, a bayonet type fitting, etc. The couplings 6 and 14 may also be a threaded coupling.

A cavity 16 is formed between the housing 12 and the coupling 14. Disposed within the cavity are a first connector 18, a second connector 20 and a data connector 22. The first connector 18 is adapted and configured to non-rotatably couple to a complementary first connector of the second coupling 6 of the driver device, and the second connector 20 is adapted and configured to non-rotatably couple to a complementary second connector of the second coupling 6 of the driver device. The complimentary first and second connectors of the second coupling 6 are non-rotatably secured to the first drive shaft 152 and the second drive shaft 154, respectively, of the flexible shaft 5. Thus, when the flexible shaft 5 is coupled to the electro-mechanical driver device 1 that includes the motor system, the motor system drives the first connector 18 and the second connector 20 via the first drive shaft 152 and the second drive shaft 154 and the complimentary first and second connectors of the second coupling 6. The data connector 22 is adapted and configured to electrically and logically connect to a complementary data connector of the second coupling 6 of the driver device. The data connector of the second coupling 6 is electrically and logically connected to the control system of the electro-mechanical driver device 1 via the data transfer cable 164. A hollow surgical cannula 24 extends distally from the housing 12 and is tapered at its distal end 26. A trocar 28 also extends distally from the housing 12 and is contained concentrically within the cannula 24, as more fully described below. The distal end 26 of the cannula 24 also includes an aperture, through which the trocar 28 may be extended, as more fully described below.

Figure 3A:
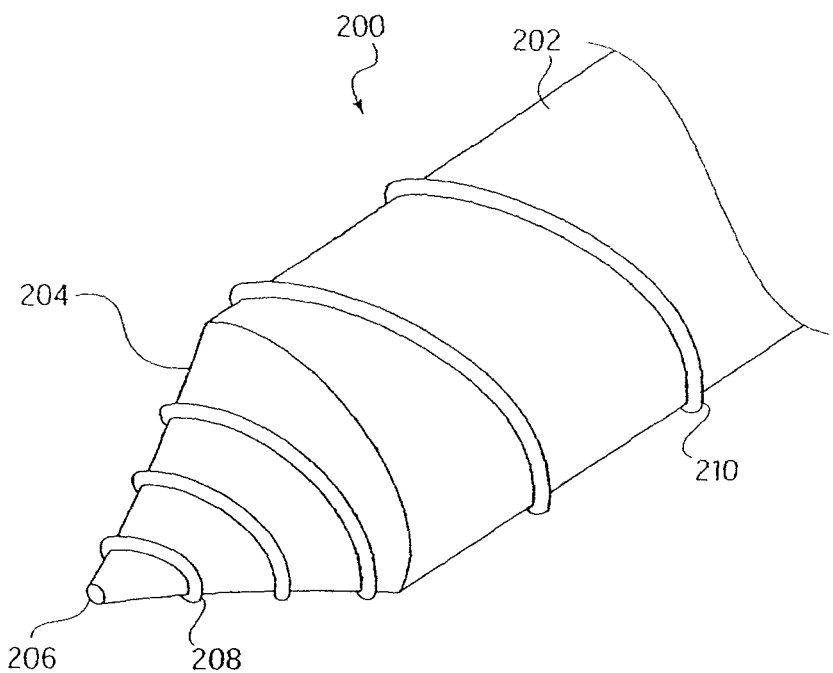
FIG. 3A is a perspective view of a first example embodiment of a trocar device according to the present invention.
Figure 3B:
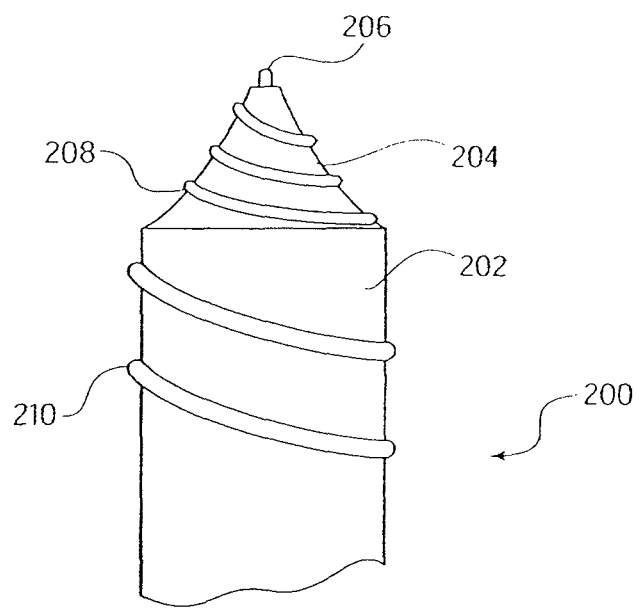
FIG. 3B is a side elevational view of the first example embodiment of the trocar device illustrated in FIG. 3A.

Referring now to FIG. 3A, there is seen a perspective view of a first example embodiment of a trocar device 200. The trocar device 200 includes a surgical cannula 202, an auger 204 disposed concentrically within the cannula 202 and a sensing tip 206 disposed concentrically within the auger 204. FIG. 3B is a side elevational view of the trocar device 200. As illustrated in FIGS. 3A and 3B, the auger 204 is provided with cutting threads 208, and the cannula 202 is provided with atraumatic, i.e., non-cutting, threads 210. The cutting threads 208 and/or the atraumatic threads 210 may be, for example, helical threads, progressive threads, a combination of thread designs, etc.

Figure 3C:
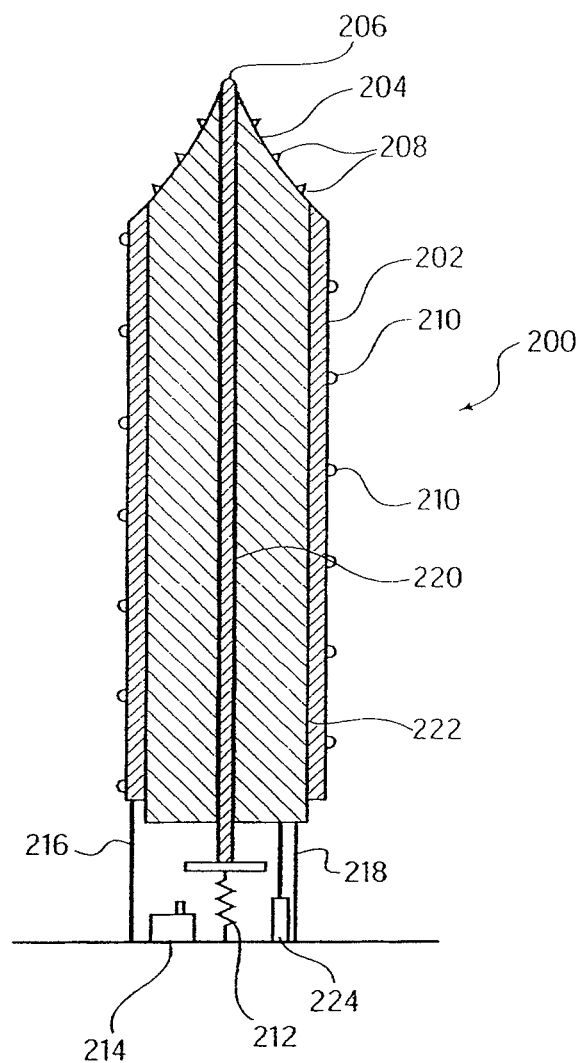
FIG. 3C is a cross-sectional schematic view of the first example embodiment of the trocar device illustrated in FIGS. 3A and 3B.

Referring now to FIG. 3C, there is seen a cross-sectional schematic view of the trocar device 200 illustrated in FIGS. 3A and 3B. As illustrated in FIG. 3C, the sensing tip 206 is disposed within a bore 220 of the auger 204 and arranged concentrically with respect to the auger 204. The distal end of the sensing tip 206 extends from the distal end of the auger 204. The proximal end of the sensing tip 206 is connected to a spring element 212, which urges the sensing tip distally with respect to the auger 204. A switch 214 is provided for detecting proximal movement of the sensing tip 206, as more fully set forth below.

The auger 204 is disposed within a bore 222 of the cannula 202 and concentrically with respect to the cannula 202. The distal end of the auger 204, in its fully extended position, is configured to extend beyond the distal end of the cannula 202, as illustrated in FIGS. 3A to 3C. Each of the cannula 202 and the auger 204 is connected with a respective driving element 216, 218, the arrangement and operation of which are described below. The auger 204 is also provided with a torque sensor, which is further described below.

Figure 4A:
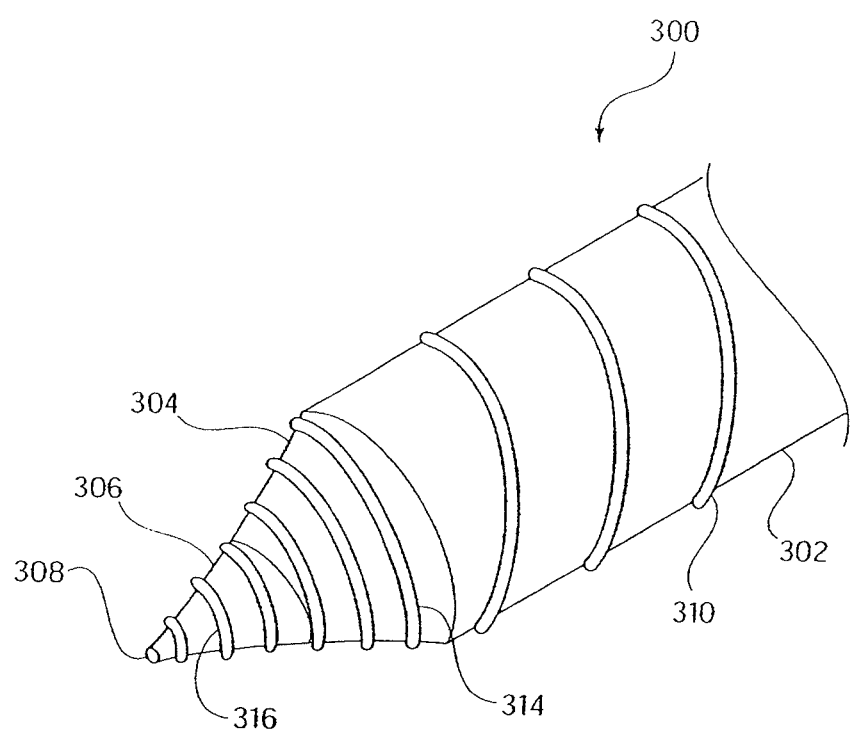
FIG. 4A is a perspective view of a second example embodiment of a trocar device according to the present invention.
Figure 4B:
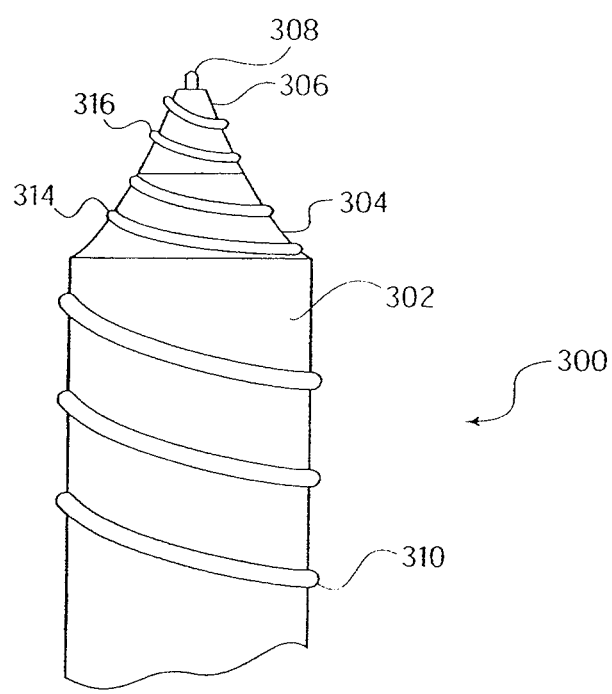
FIG. 4B is a side elevational view of the second example embodiment of the trocar device illustrated in FIG. 4A.

Referring now to FIG. 4A, there is seen a perspective view of a second example embodiment of a trocar device 300 according to the present invention. As seen in FIG. 4A, the trocar device 300 includes a surgical cannula 302 having atraumatic threads 310, an external auger 304 having cutting threads 314, an internal auger 306 having cutting threads 316 and a sensing tip 308. FIG. 4B is a side elevational view of the trocar device 300 illustrated in FIG. 4A. It should be appreciated that the atraumatic threads 310, the cutting threads 314 and/or the cutting threads 316 may be, for example, helical threads, progressive threads, a combination of thread designs, etc.

Figure 4C:
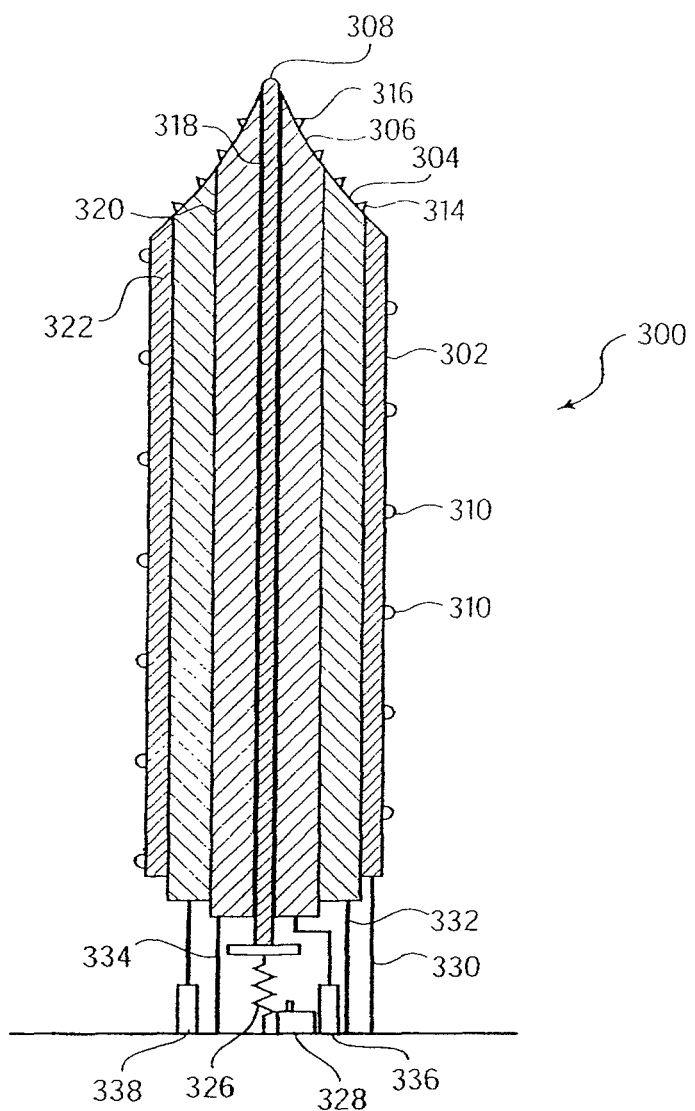
FIG. 4C is a cross-sectional schematic view of the second example embodiment of the trocar device illustrated in FIGS. 4A and 4B.

Referring now to FIG. 4C, there is seen a cross-sectional schematic view of the trocar device 300 illustrated in FIGS. 4A and 4B. The sensing tip 308 is disposed within a bore 318 of the internal auger 306 and is arranged concentrically with respect to the internal auger 306. The internal auger 306 is disposed within a bore 320 of the external auger 304 and is arranged concentrically with respect to the external auger 304. The external auger 304 is disposed within a bore 322 of the cannula 302 and is arranged concentrically with respect to the cannula 302.

As illustrated in FIG. 4C, the distal end of the sensing tip 308, in its fully extended position, extends from the distal end of the internal auger 306. The proximal end of the sensing tip 308 is connected to a spring element 326, which urges the sensing tip 308 distally with respect to the internal auger 306. A switch 328 is provided for detecting the proximal movement of the sensing tip 308. In its fully extended position, the distal end of the internal auger 306 extends from the distal end of the external auger 304, and, in its fully extended position, the distal end of the external auger 304 extends from the distal end of the cannula 302. It should be appreciated that FIG. 4C illustrates the internal auger 306 and the external auger 304 in their fully extended positions. Each of the cannula 302, the external auger 304 and the internal auger 306 is connected to a respective driving element 330, 332, 334. The internal auger 306 is provided with a torque sensor 336, and the external auger 304 is provided with a torque sensor 338, both of which are described below.

It should be understand that FIGS. 3C and 4C illustrate the trocar device 200, 300 schematically and that the driving elements 216, 218 of the trocar device 200 and the driving elements 330, 332, 334 of the trocar device 300 may be provided in the housing 12 of the trocar device 200, 300, in the electro-mechanical driver device 1 or a combination thereof. Similarly, the torque sensors 224, 336, 338 may be provided within the housing 12 of the trocar device 200, 300, in the electro-mechanical driver device 1 or a combination thereof. Regardless of the location of the driving elements 216, 218, 330, 332, 334 and the torque sensors 224, 336, 338, it should be appreciated that the driving elements 216, 218, 330, 332, 344 are operated by the operator via the control system of the electro-mechanical driver device 1 and that the output of the torque sensors 224, 336, 338 is used by the control system of the electro-mechanical driver device 1 to control the operation of the trocar device 200, 300, as more fully described below.

Figure 5A:
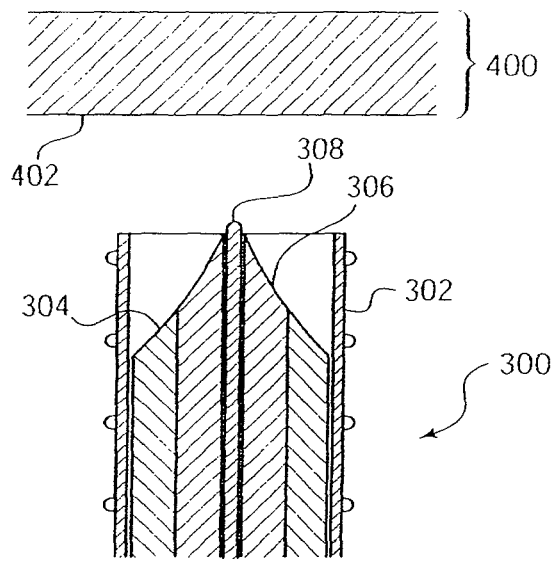
FIGS. 5A to 5H illustrate an operation sequence of the trocar device illustrated in FIGS. 4A to 4C.

Referring now to FIGS. 5A to 5H, there is seen an operational sequence of the trocar device 300 illustrated in FIGS. 4A to 4C. The trocar device 300 or portions thereof may be sterilized sometime prior to use. FIG. 5A illustrates the trocar device 300 prior to contacting the surface 402 of tissue 400 (e.g., human or animal). As illustrated in FIG. 5A, the internal auger 306 and the external auger 304 have been substantially retracted into the cannula 302. At least a portion of the sensing tip 308 is arranged to extend from the distal end of the cannula 302. A distal end portion of the internal auger 306 may also be configured to extend from the distal end of the cannula 302 when the trocar device 300 is in the condition prior to contacting the surface 402 of the tissue 400 as illustrated in FIG. 5A.

Figure 5B:
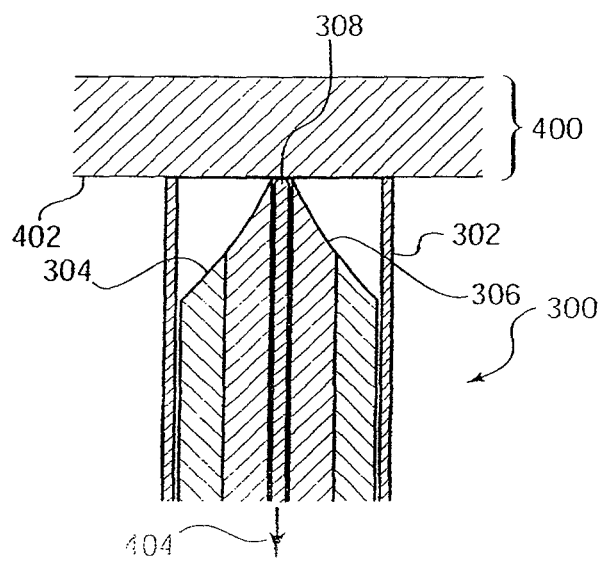
Figure 5C:
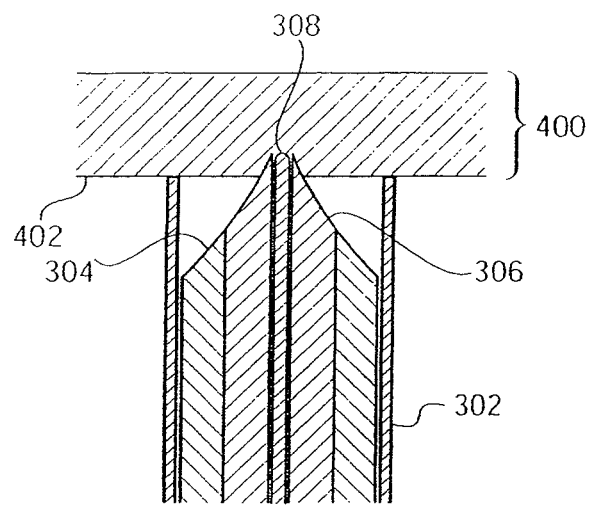

As illustrated in FIG. 5B, the trocar device 300 is located at the intended point of incision and pressed against the surface 402 of the tissue 400. The sensing tip 308 is caused to be displaced in the direction of the arrow 404 by the pressing of the trocar device 300 against the surface 402 of the tissue 400. The displacement of the sensing tip 308 causes the state of the switch 328 to change from ON to OFF or vice versa depending on whether switch 328 is configured as a normally-closed or normally-open switch. The change of state of the switch 328 signals the control system of the electro-mechanical driver device 1 that the trocar device 300 is in position against the surface 402 of the tissue 400. Until the control system determines that the trocar device 300 is in position against the surface 402 of tissue 400, in accordance with the state of switch 328, the control system prevents the operation of the driving elements 330, 332, 334. In addition, the control system does not activate the driving elements 330, 332, 334 until the appropriate control element 34, 36 of RCU 30 has been activated by the operator. Thus, the driving elements 330, 332, 334 are not activated until the trocar device 300 is in position and the appropriate control element 34, 36 has been activated.

After the trocar device 300 is placed in position against the surface 402 of tissue 400 and the operator has activated the appropriate control element 34, 36, the control system of the electro-mechanical driver device 1 activates the driving element 330 to rotate the cannula 302, the driving element 332 to rotate the external auger 304 and the driving element 334 to rotate the internal auger 306. In addition to rotating the internal auger 306 and the external auger 304, the driving elements 332, 334 advance or extend the respective auger 304, 306 in accordance with the rotation and thread pitch thereof. During rotation of the internal auger 306 and the external auger 304, the torque sensors 336, 338 respectively output a signal to the control system of the electro-mechanical driver device 1 in accordance with the torque required to continue the rotation and advancement of the internal auger 306 and the external auger 304. It should be appreciated that the cutting threads 316 of the internal auger 306 and the cutting threads 314 of the external auger 304 are configured to cut into the tissue 400 as well as to draw the tissue 400 proximally there along.

Figure 5D:
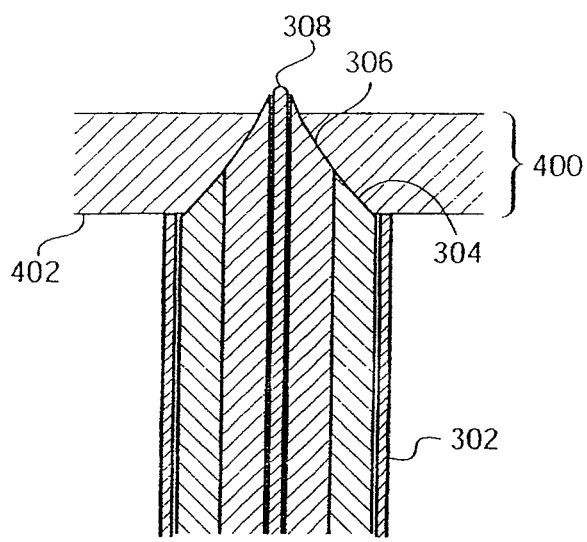

The control system of the electro-mechanical driver device 1 continues the rotation of the internal auger 306, the external auger 304 and the cannula 302 and the extension of the internal auger 306 and the external auger 304 until it is determined that the internal auger 306 has traversed the tissue 400. This determination is made in accordance with the output of the torque sensor 336. That is, the torque required to continue the rotation and extension of the internal auger 306 will decrease at the time that the distal end of the internal auger 306 has fully traversed the tissue 400. The trocar device 300 is illustrated in FIG. 5D in the condition and position where the internal auger 306 has fully traversed the tissue 400.

In response to this condition, the control system of the electro-mechanical driver device 1 continues the rotation of the external auger 304 and the cannula 302 and the extension of the external auger 304 but causes the retraction of the internal auger 306 into the bore 320 of the external auger 304. The retraction of the internal auger 306 may be performed with or without the rotation of the internal auger 306 in accordance with the design and arrangement of the driving element 334. The control system of the electro-mechanical driver device 1 causes the continued retraction of the internal auger 306 until it has reached its fully retracted position in the bore 320 while simultaneously continuing the rotation of the external auger 304 and cannula 302 and the extension of the external auger 304. Once the external auger 304 has incised the tissue 400 to its maximum diameter, at which time the external auger 304 has been fully extended from the cannula 302, the atraumatic threads 310 of the cannula 302 draw the cannula 302 into the tissue 400.

Figure 5E:
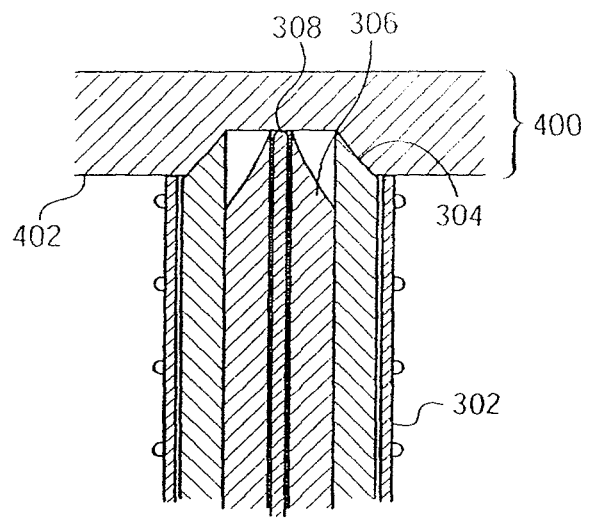
Figure 5F:
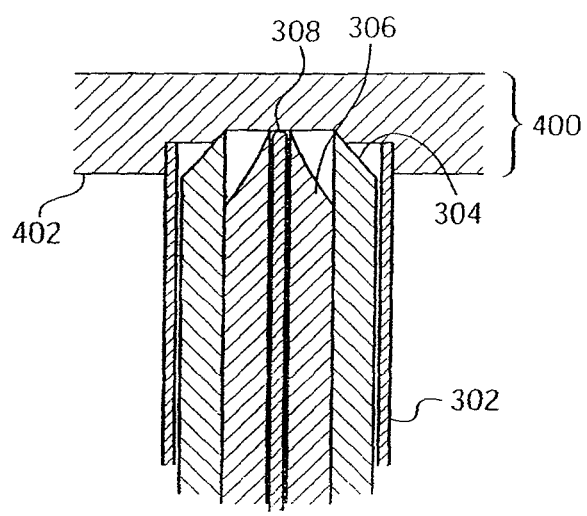

The torque sensor 338 of the external auger 304 outputs a signal to the control system of the electro-mechanical driver device 1 during this operation. In response to the external auger 304 reaching its maximum extension from the cannula 302, the torque necessary to continue the rotation of the external auger 309 will decrease. This condition, as determined by control system of the electro-mechanical driver device 1 in accordance with the output from the torque sensor 338, causes the control system to retract the external auger 304 relative to the cannula while continuing to rotate the cannula 302. FIG. 5E illustrates the trocar device 300 in the position in which the external auger 304 has reached its maximum extension from the cannula 302.

Figure 5G:
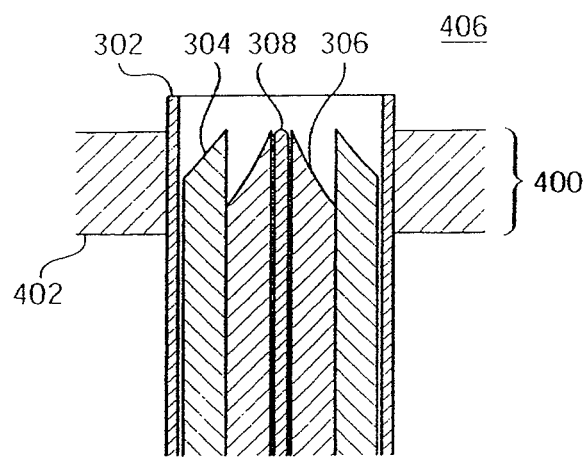
Figure 5H:
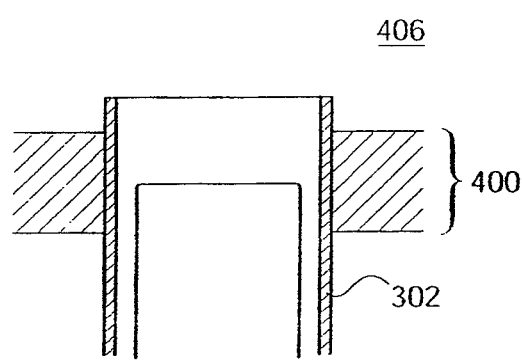

After having reached its maximum extension, the control system of the electro-mechanical driver device 1 causes the external auger 304 to retract relative to the cannula 302 while continuing the rotation of the cannula 302 to draw the cannula 302 into the incision by the atraumatic threads 310 thereof. The retraction of the external auger 309 may be performed with or without rotation thereof in accordance with the design and configuration of the driving element 332. The continued rotation of the cannula 302 draws the cannula 302 into the tissue 400 until the distal end of the cannula 302 has at least traversed the tissue 400. The cannula 302 may be further rotated to draw the cannula 302 an additional length into the cavity 406 as illustrated in FIG. 5G. Once the control system of the electro-mechanical driver device 1 has determined that the cannula 302 has been fully inserted into the tissue 400, the driving element 330 is deactivated, thereby stopping the rotation, and the advancement, of the cannula 302. The internal auger 306 and the external auger 304 are subsequently withdrawn from the cannula 302 to thereby provide access to the cavity 406 by an instrument 408 via the cannula 302 as illustrated in FIG. 5H. It will be appreciated that a seal may be provided, for example, at the proximal end of the cannula 302, to provide a fluid-tight and/or gas-tight seal between the cavity 406 and the environment.

After the cannula 302 has reached its operable position, as shown in FIGS. 5G and 5H, the cannula 302 may be removed from the housing 12, to thereby provide access to the cavity 406 via the cannula 302. Alternatively, the housing 12 may be provided with a port to provide access to the cavity 406 via the cannula 302.

After the procedure has been completed, the control system of the electro-mechanical driver device 1 may be controlled by, for example, a control element 34, 36 of RCU 30, to rotate the cannula 302 to cause the retraction of the cannula 302 from the tissue 400.

Figure 6A:
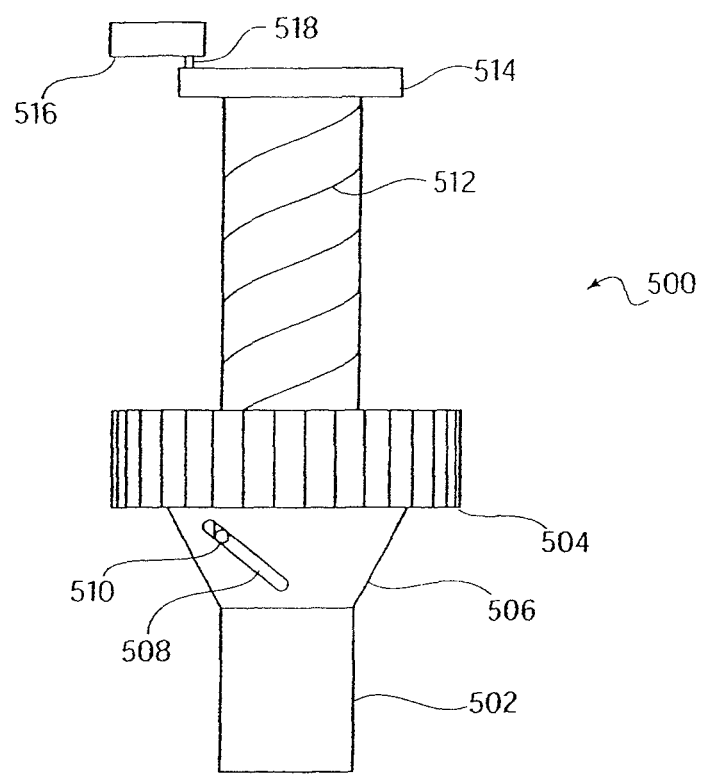
FIGS. 6A and 6B illustrate a first example embodiment of a torque sensor of the trocar device according to the present invention.
Figure 6B:
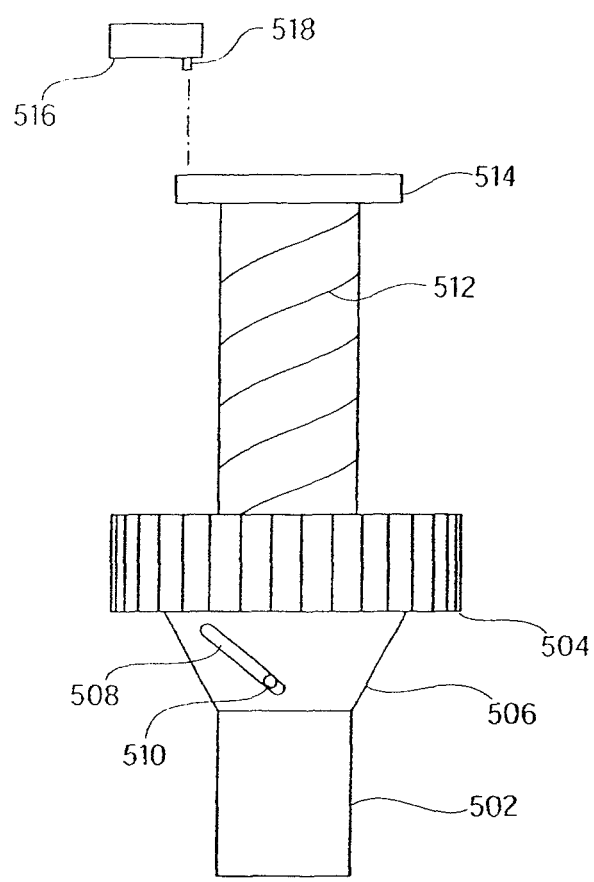

Referring now to FIGS. 6A and 6B, there is seen two side schematic views of a first example embodiment of a torque sensor 500. Torque sensor 500 is illustrated in FIGS. 6A and 6B as being configured to measure the torque necessary to drive the shaft 502. The shaft 502 may correspond to, for example, the auger 204 of the trocar device 200, the internal auger 306 of the trocar device 300, the external auger 304 of the trocar device 300, etc. The shaft 502 includes a gear 504 secured thereto that is driven by the driving element corresponding to the shaft 502. A spring element 512 is provided on one side of gear 504 and secured to the shaft 502 by cap element 514. The side of gear 504 opposite to spring element 512 is provided with a collar 504, which is non-rotatably secured to the gear 504. The collar 506 is provided with a slot 508, and the shaft 502 is provided with a pin 510 slidably disposed in the slot 508. The torque sensor 500 further includes a switch element 516, which includes an actuator 518. Switch 516 may be a normally-open switch or a normally-closed switch. FIG. 6A illustrates the shaft 502 and torque sensor 500 in a low torque condition, in which the spring element 512 urges the cap element 514 against the actuator 518 of switch element 516. However, when the torque necessary to drive the shaft 502 exceeds a predefined threshold, in accordance with, for example, the spring constant of spring element 512, the pin 510 is urged along the slot 508, overcoming the force of spring element 512. The longitudinal displacement component causes the shaft 502 to translate relative to the switch element 516, thereby releasing the actuator 518. The release of actuator 518 causing the state of switch element 516 to change from ON to OFF or vise versa in accordance with the torque requirement exceeding the predefined threshold. FIG. 6B illustrates the condition that the torque requirement for driving shaft 502 has exceeded the predefined threshold.

Figure 7:
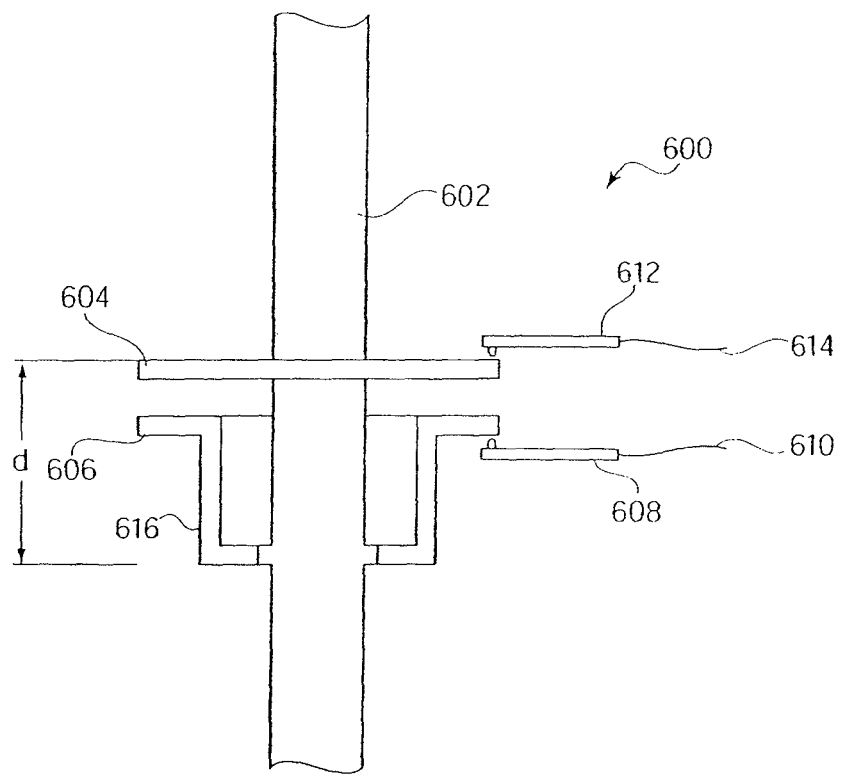
FIG. 7 is a schematic view of a second example embodiment of a torque sensor of the trocar device according to the present invention.

Referring now to FIG. 7, there is seen a schematic view of a second example embodiment of a torque sensor 600 of the trocar device according to the present invention. The torque sensor 600 is configured to measure the torque necessary to drive a shaft 602, which may correspond to, for example, the auger 204 of the trocar device 200, the internal auger 306 of the trocar device 300, the external auger 304 of the trocar device, 300, etc. The torque sensor 600 includes a first disk 604 secured to the shaft 602 at a first location along the length thereof and a second element 616 secured to the shaft 602 at a second location thereof. The second element 616 includes a flange 606. As illustrated in FIG. 7, the first location is spaced from the second location at a distance d. Each of the first disk 604 and the flange 606 includes a series of radially-spaced apertures having predefined areas. In a zero-torque condition of the shaft 602, the apertures of the first disk 604 are aligned with the apertures of the flange 606. A light source 608, which is powered by line 610, and a light sensor 612, which outputs a signal via line 614, are arranged on opposite sides of the first disk 604 and the flange 606. The light sensor 612 may be configured, for example, to output a signal in accordance with an intensity of light received thereby from light source 608. As the torque required to drive shaft 602 increases, the alignment of the apertures of first disk 604 relative to the apertures of flange 606 is shifted. Thus, the area of the resultant aperture decreases in accordance with an increasing torque requirement. This area change is measurable by the light sensor 612 in accordance with the resultant change of light intensity being transmitting by the light source 608 to the light sensor 612.

Figure 8A:
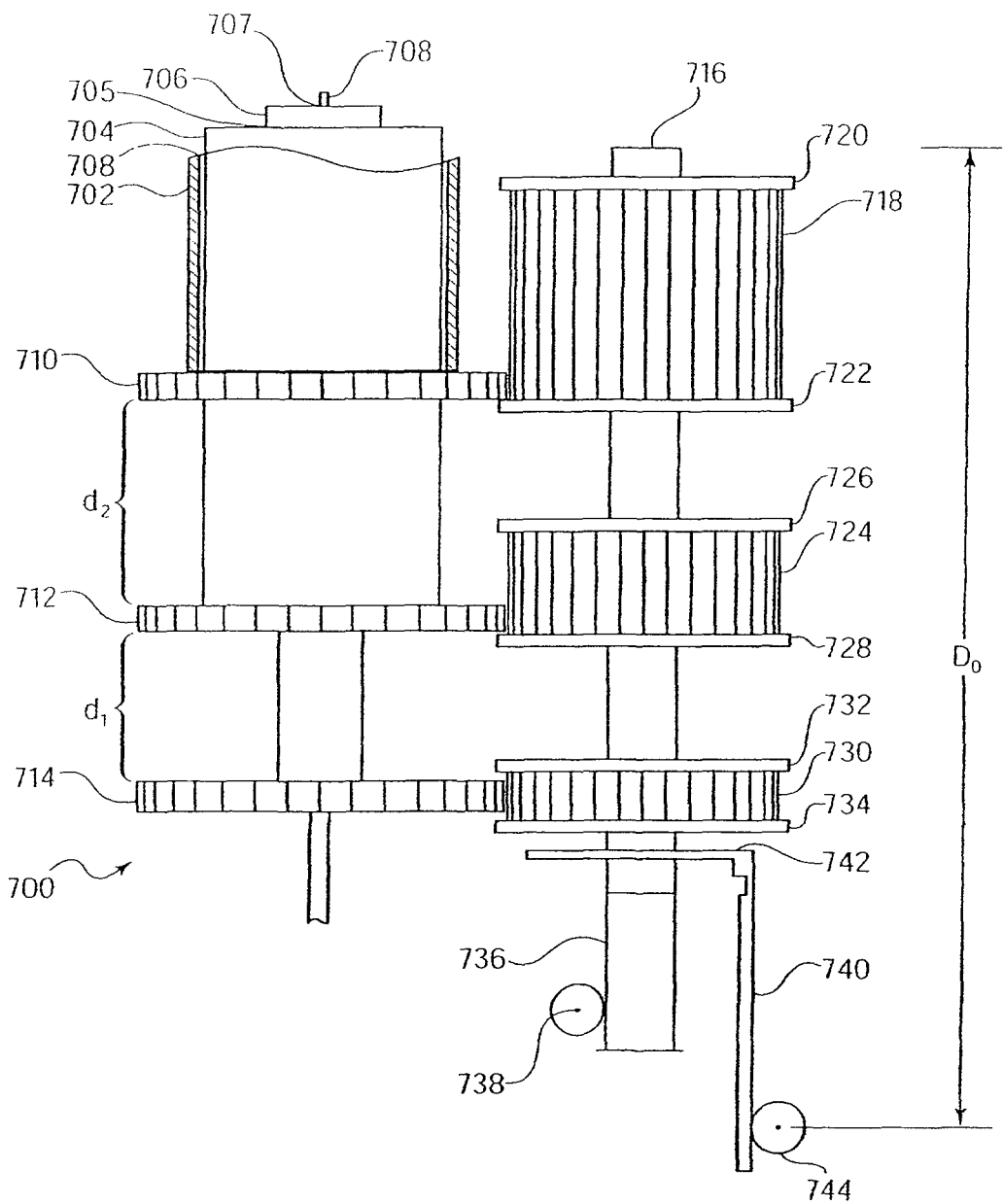
FIGS. 8A to 8C are schematic views of a first example embodiment of a driving device of the trocar device according to the present invention.
Figure 8B:
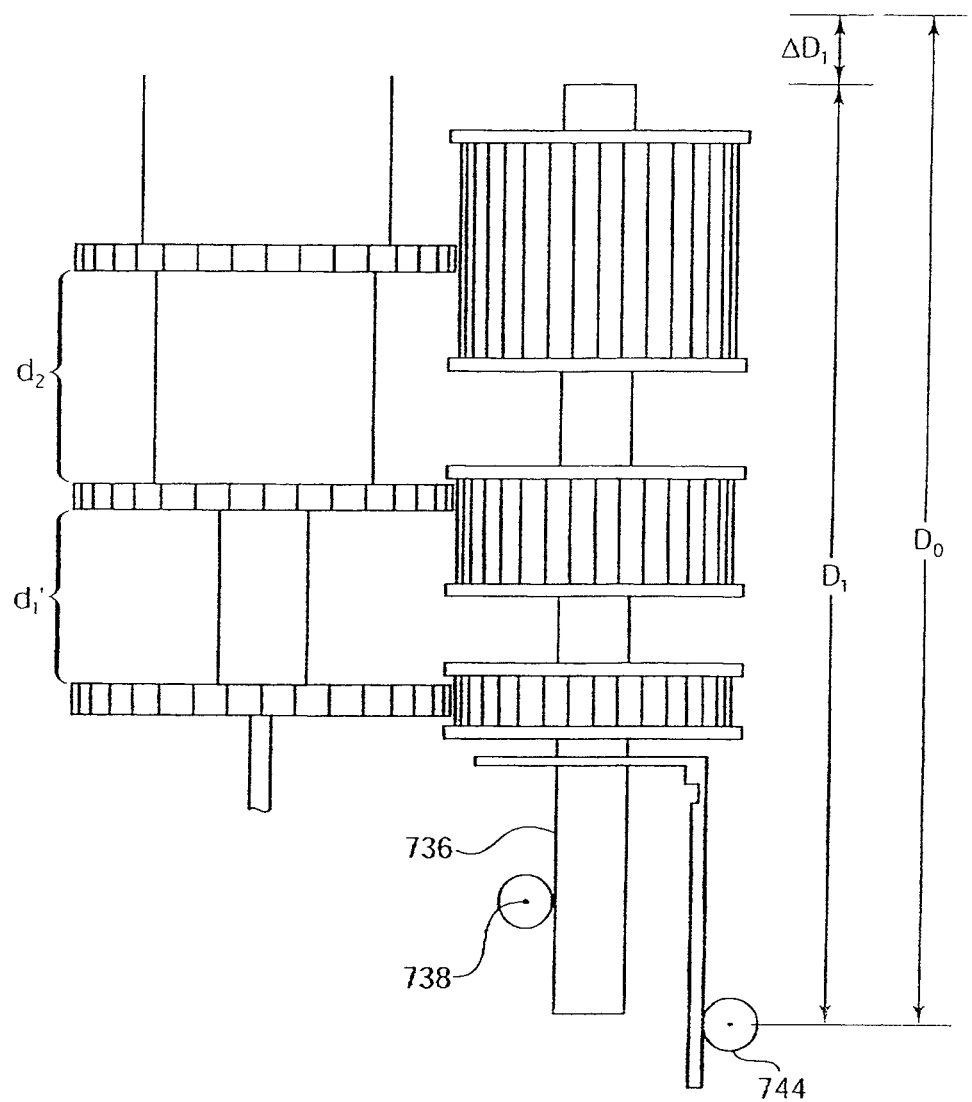
Figure 8C:
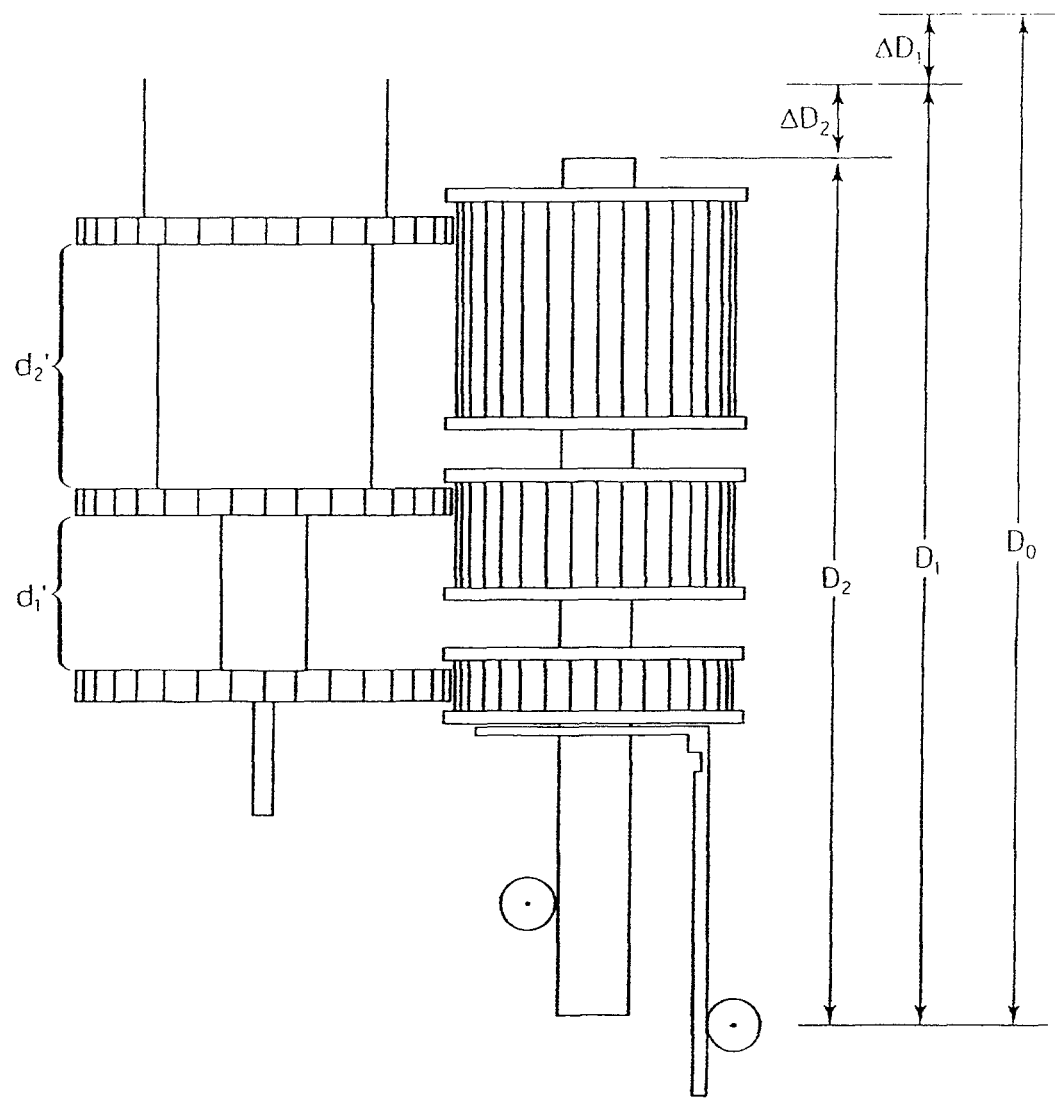

FIGS. 8A to 8C illustrate schematically a first example embodiment of a driving device 700 of the trocar device according to the present invention. The driving device 700 is configured to perform the rotation of and the extension and retraction of the several shafts 702, 704, 706. As illustrated in FIG. 8A, a first shaft 706 is disposed concentrically and rotatably within a bore 705 of a second shaft 704, and the second shaft 704 is disposed concentrically and rotatably within a bore 703 of a third shaft 702. The first shaft 706 may correspond to the internal auger 306 of the trocar device 300, the second shaft 704 may correspond to the external auger 304 of the trocar device 300, and the third shaft 702 may correspond to the cannula 302 of the trocar device 300. A fourth shaft 708 may be disposed within a bore 707 of the first shaft 706. The fourth shaft 708 may correspond to the sensing tip 308 of the trocar device 300. It should be appreciated that any appropriate number of shafts may be provided in the driving device 700 and that the number of shafts illustrated in FIGS. 8A to 8C is merely intended to be exemplary. A first gear 714 is non-rotatably provided at the proximal end of the first shaft 706, a second gear 712 is non-rotatably provided at the proximal end of the second shaft 704, and a third gear 710 is non-rotatably provided at the proximal end of the third shaft 702.

The driving device 700 further includes a rotatable and axially displaceable driveshaft 716. The driveshaft 716 includes a first gear 730; a second gear 724 and a third gear 718, each of which is non-rotatably secured to the driveshaft. Each of the first gear 730, the second gear 724 and the third gear 718 is rotatable and axially displaceable in accordance with the rotation of the driveshaft 716 and the axial displacement thereof. It should be appreciated that the first gear 730 and the first gear 714 are engageable so that the rotation of the driveshaft 716 causes the rotation of the first shaft 706. Similarly, the second gear 724 is engageable with the second gear 712 so that the rotation of the driveshaft 716 causes rotation of the second shaft 704, and the third gear 718 is engageable with the third gear 710 so that rotation of the driveshaft 716 causes rotation of the third shaft 702. It should be appreciated that the gear ratios will determine the relative rotation between the first shaft 706, the second shaft 704 and the third shaft 702. As illustrated in FIGS. 8A to 8C, the gear ratios between the first gear pair 714, 730, the second gear pair 712, 724 and the third gear pair 710, 718 may be the same so that the first shaft 706, the second shaft 704 and the third shaft 702 rotate synchronously in accordance with the rotation of the driveshaft 716.

The proximal end of the driveshaft 716 is provided with a gear 736, which is drivable by a driveshaft 738, the rotation of which effects the rotation of the driveshaft 716. The gear 736 may be, for example, a worm gear, a spur gear, etc. The proximal end of the driveshaft 716 is also provided with a rack 740 via mount 742. The driveshaft 716 is rotatably secured to the mount 742 and axially displaceable therewith. A pinion 744 is provided for axially displacing the mount 742, and therefore the driveshaft 716 and gears 718, 724, 730, via the rack 740.

The first gear 730 includes a distal shoulder 732 and a proximal shoulder 734 that engage the distal and proximal surfaces of the first gear 714 to effect axial displacement of the first shaft 706 as more fully described below. The second gear 724 includes a distal shoulder 726 and a proximal shoulder 728 that engage the distal and proximal surfaces of second gear 712 to effect the axial displacement of the second shaft of 704 as more fully described below. Similarly, the third gear 718 includes a distal shoulder 720 and a proximal shoulder 722 that engage the distal and proximal surfaces of the third gear 710 to effect the axial displacement of the third shaft 702 and/or to act as positive stops for driving device 700.

As seen in FIGS. 8A to 8C, the height of the first gear 730, i.e., the distance between the distal shoulder 732 and the proximal shoulder 734, is substantially equal to the height of the first gear 714. That is, there is substantially zero axial clearance between the shoulders 732, 734 and the distal and proximal surfaces of first gear 714. The height of the second gear 724, i.e., the distance between the distal shoulder 726 and the proximal shoulder 728, is elongated as compared to the height of the first gear 730, and the height of the third gear 718, i.e., the distance between the distal shoulder 720 and the proximal shoulder 722, is elongated as compared to the height of the first gear 730 and the height of the second gear 724. As will be apparent from the following description, the heights of the gears 730, 724, 718 define the stroke of the respective shaft 706, 704, 702.

FIG. 8A illustrates the first shaft 706 and the second shaft 704 in their fully extended positions. The distance between the first gear 714 and the second gear 712 is represented in FIG. 8A as $d_1$, the distance between the second gear 712 and the third gear 710 is represented in FIG. 8B as $d_2$, and the distance between the pinion 744 and the distal end of the driveshaft 716 is represented as $D_0$. It should be understood that these distances are only referred to herein for clarity purposes and to illustrate the relative displacement of the elements of the driving device 700 as more fully set forth below.

Referring now to FIG. 8B, there is seen a schematic view of the driving device 700 in which the pinion 744 has effected an axial displacement of the driveshaft 716 by a distance $\Delta D_1$ so that the distance between the pinion 744 and the distal end of the driveshaft 716 is represented by $D_1$. As illustrated in FIG. 8B, the first shaft 706 has been displaced to its fully retracted position relative to the second shaft 704. That is, the axial displacement of the first gear 730, in accordance with the operation of pinion 744, causes axial displacement of the first gear 714 by the interaction of the distal shoulder 732 of the first gear 730 with the distal surface of the first gear 714. The height of the second gear 724 and the height of the third gear 718 permit the second shaft 704 and the third shaft 702 to remain stationary in the axial direction during this stroke of the first shaft 706. In the position as illustrated in FIG. 8B, the distance between the first gear 714 and the second gear 712 has increased from $d_1$ to $d_1'$ while the distance between the second gear 712 and the third gear 710 has remained substantially at $d_2$. It should be appreciated that the value of $d_1'$ is substantially equal to the sum of the values $d_1$ and $\Delta D_1$ and that the axial displacement of the first shaft 706 relative to the second shaft 704 is substantially equal to the value $\Delta D_1$.

Referring now to FIG. 8C, there is seen a schematic view of the driving device 700 in which the pinion 744 has effected a further axial displacement of the driveshaft 716 by an additional distance of $\Delta D_2$, so that the distance between the pinion 744 and the distal end of the drive shaft 716 is represented by $D_2$. As illustrated in FIG. 8C, the first shaft 706 remains in its fully retracted position relative to the second shaft 704, and the second shaft 704 has been displaced to its fully retracted position relative to the third shaft 702. That is, the axial displacement of the first gear 730, in accordance with the operation of the pinion 744, causes further axial displacement of the first gear 714 by the interaction of the distal shoulder 732 of the first gear 730 with the distal surface of the first gear 714. Furthermore, the axial displacement of second gear 724, in accordance with the operation of the pinion 744, causes axial displacement of the second gear 712 by the interaction of the distal shoulder 726 of the second gear 724 with the distal surface of the second gear 710. The height of the third gear 718 permits the third shaft 702 to remain stationary in the axial direction during this stroke of the first shaft 706 and the second shaft 704. Alternatively, the height of the third gear 718 may define the positive steps for the axial displacement of the drive shaft 716. In the position as illustrated in FIG. 8C, the distance between the first gear 714 and the second gear 712 has remained substantially equal to $d_1'$ while the distance between the second gear 712 and the third gear 710 has increased from $d_2$ to $d_2'$. It should be appreciated that the value of $d_2'$ is substantially equal to the sum of the values of $d_2$ and $\Delta D_2$ and that the axial displacement of the second shaft 704 relative to the third shaft 702 is substantially equal to the value of $\Delta D_2$. It should also be appreciated that although the relative axial distance between the first shaft 706 and the second shaft 704 has remained substantially the same between the positions illustrated in FIGS. 8B and 8C, the first shaft 706 is axial displaced relative to the third shaft 702 by a distance substantially equal to the value of $\Delta D_2$. That is, the total axial displacement of the first shaft 706 relative to the third shaft 702 between the position illustrated in FIG. 8A and the position illustrated in FIG. 8C is substantially equal to the sum of the values of $\Delta D_1$ and $\Delta D_2$.

If should be appreciated that although FIGS. 8A to 8C illustrated the retraction of the first shaft 706 and the second shaft 704 in sequence, the first shaft 706 and second shaft 704 are extendable by reversing the sequence, i.e., operating the pinion 744 to extend the drive shaft 716. It should also be appreciated that the heights of the gears 730, 724, 718 define the strokes of the first shaft 706 and the second shaft 704. While a rack 740 and pinion 744 are described above for axially displacing the drive shaft 716, any device suitable for effecting axial displacement, such as, for example, a solenoid, a linear motor, alternative gearing arrangements, etc., may be used. In addition, the first gear pair 714, 730, the second gear pair 712, 724 and/or the third gear pair 710, 718 may be, for example, spur gears, helical gears, etc.

Figure 9:
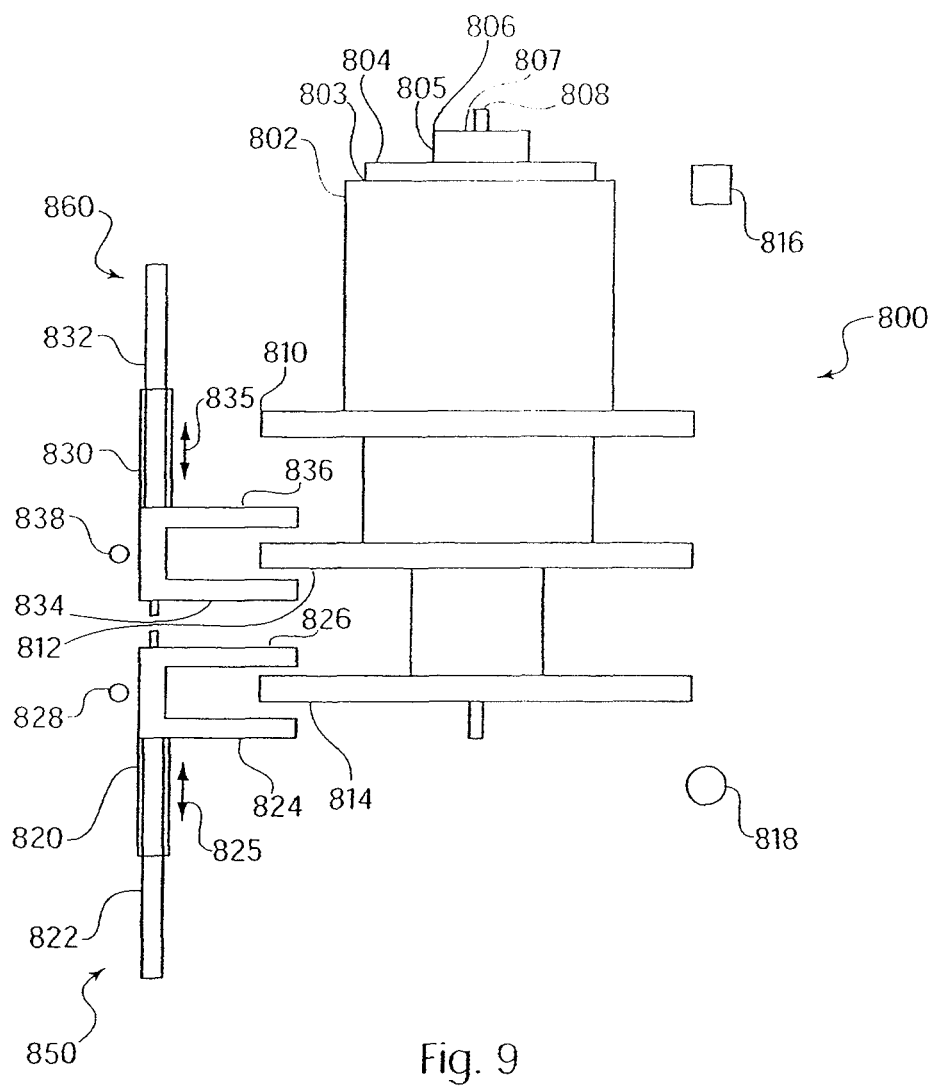
FIG. 9 is a schematic view of a second example embodiment of a driving device of the trocar device according to the present invention.

Referring now to FIG. 9, there is seen a schematic view of a second example embodiment of a driving device 800 of the trocar device according to the present invention. The driving device 800 is configured to rotate a first shaft 806, which is concentrically and rotatably disposed in a bore 805 of a second shaft 804, to rotate the second shaft 804, which is concentrically and rotatably disposed in a bore 803 of a third shaft 802 and to rotate the third shaft 802. The driving device 800 is also configured to axially displace the first shaft 806 and the second shaft 804. A fourth shaft 808 is illustrated in FIG. 9 as being concentrically disposed within a bore 807 of the first shaft 806. It should be appreciated that the driving device 800 may be configured to rotate any number of shafts and to axially displace any one or more of such shafts.

A first gear 814 is non-rotatably provided at the proximal end of the first shaft 806, a second gear 812 is provided at the proximal end of the second shaft 804, and a third gear 810 is provided at the proximal end of the third shaft 802. Each of the first gear 814, the second gear 812 and the third gear 810 is arranged and configured to be rotated in accordance with the rotation of a drive shaft 816. The gears 814, 812, 810 and drive shaft 816 may be configured, for example, as spur gears, helical gears, etc. The drive shaft 816 may be rotated by a driving element 818, which may include, for example, a motor.

The driving device 800 further includes a first linear actuator 850 configured to axially displace the first shaft 806. The first linear actuator 850 includes a rack 820, a distal shoulder 826 and a proximal shoulder 824. The rack 820 is engageable with a pinion 828, and the rack 820, distal shoulder 826 and proximal shoulder 824 are displaceable as a unit in accordance with the operation of the pinion 828. The first gear 814 is disposed between the distal shoulder 826 and the proximal shoulder 824 to effect axial displacement thereof. The rack 820, the distal shoulder 826 and the proximal shoulder 824 are slidably disposed on stem 822.

The second linear actuator 860 includes a rack 830, a distal shoulder 836 and a proximal shoulder 834 slidably disposed and displaceable as a unit on stem 832. The displacement of the rack 830, the distal shoulder 836 and the proximal shoulder 834 by the pinion 838 effects the displacement of the second shaft 804 by the interaction of the distal shoulder 836 and the proximal shoulder 834 with the second gear 812.

Figure 10:
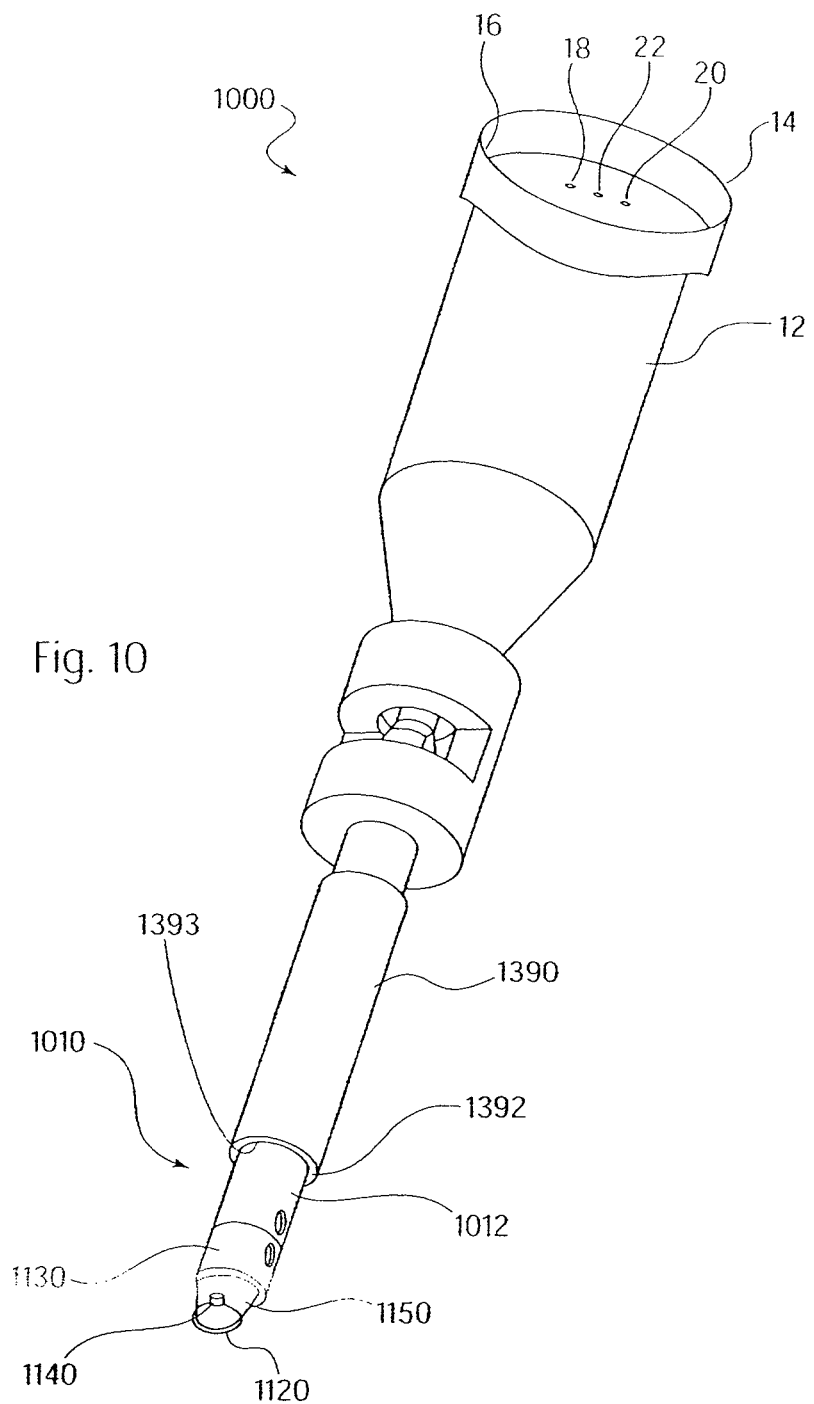
FIG. 10 is a schematic view of another example trocar device according to the present invention.

Another exemplary embodiment of the present invention is illustrated in FIG. 10. As shown in this figure, a trocar device 1000 includes a housing 12 with a coupling 14 adapted and configured to detachably couple the trocar device 1000 with, for example, the second coupling 6 of the flexible shaft 5 of the driver device. As with the auger-type trocar described above, the coupling 14 of the trocar device 1000 may be a quick-connect type fitting, such as, for example, a rotary quick-connect type fitting, a bayonet type fitting, etc. The couplings 6 and 14 may also be a threaded coupling.

As with the auger-type trocar, a cavity 16 is formed between the housing 12 and the coupling 14. Disposed within the cavity are a first connector 18, a second connector 20 and a data connector 22. The first connector 18 is adapted and configured to non-rotatably couple to the complementary first connector of the second coupling 6 of the driver device, and the second connector 20 is adapted and configured to non-rotatably couple to the complementary second connector of the second coupling 6 of the driver device. Thus, when the flexible shaft 5 is coupled to the electro-mechanical driver device 1 that includes the motor system, the motor system drives (e.g., rotates) the first connector 18 and the second connector 20 via the first drive shaft 152 and the second drive shaft 154 and the complimentary first and second connectors of the second coupling 6. The data connector 22 is adapted and configured to electrically and logically connect to the complementary data connector of the second coupling 6 of the driver device, which is electrically and logically connected to the control system of the electro-mechanical driver device 1 via the data transfer cable 164.

A cutting arrangement 1010 extends distally from the housing 12. The cutting arrangement 1010 includes a housing 1012, a blade housing portion 1130 connected to the housing 1012, a cutting blade 1120, and a pin 1140. The blade housing portion 1130 has a tapered distal end 1150 for easy insertion into an incision to be formed. The cutting blade 1120 may be rotatably connected, for example, to a tapered distal end 1150 of the blade housing portion 1130 via the pin 1140. The cutting blade 1120 may have a generally circular profile and/or a generally disk shape, for example, and may include one or a number of sharp edges and/or cutting teeth for cutting tissue (e.g., human or animal tissue).

A surgical cannula 1390 is also provided for insertion into tissue. The cannula 1390 surrounds the cutting arrangement 1010 and may be configured to be moveable and removeable (mechanically or manually) relative to the cutting arrangement 1010. The cannula 1390 may be tapered at a distal end 1392.

The distal end 1011 of the cutting arrangement 1010 extends through a bore 1393 of the cannula and beyond the distal end 1392 of the cannula 1390.

Figure 11A:
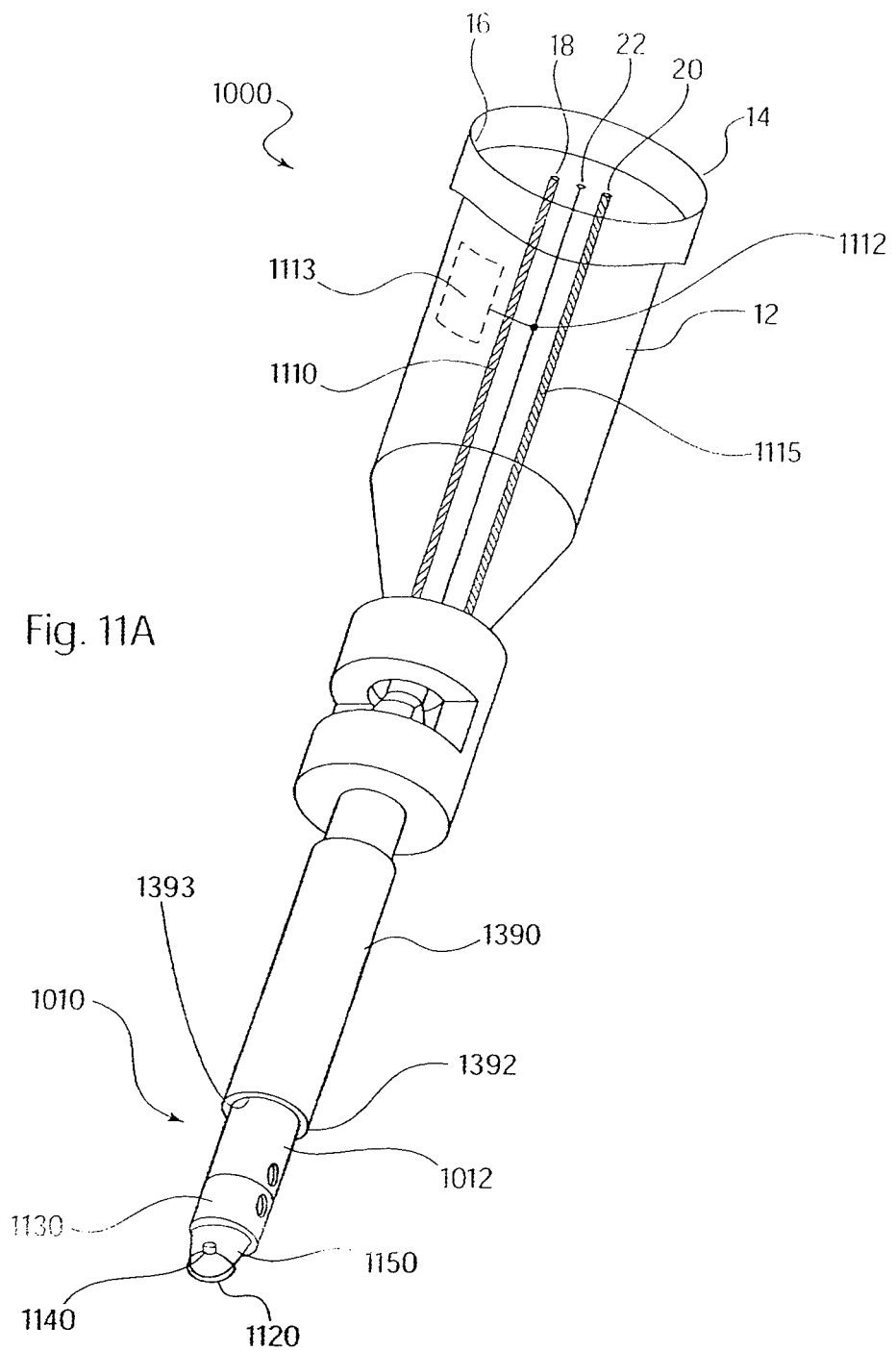
FIG. 11a is a detailed schematic view of the trocar device illustrated in FIG. 10.
Figure 11B:
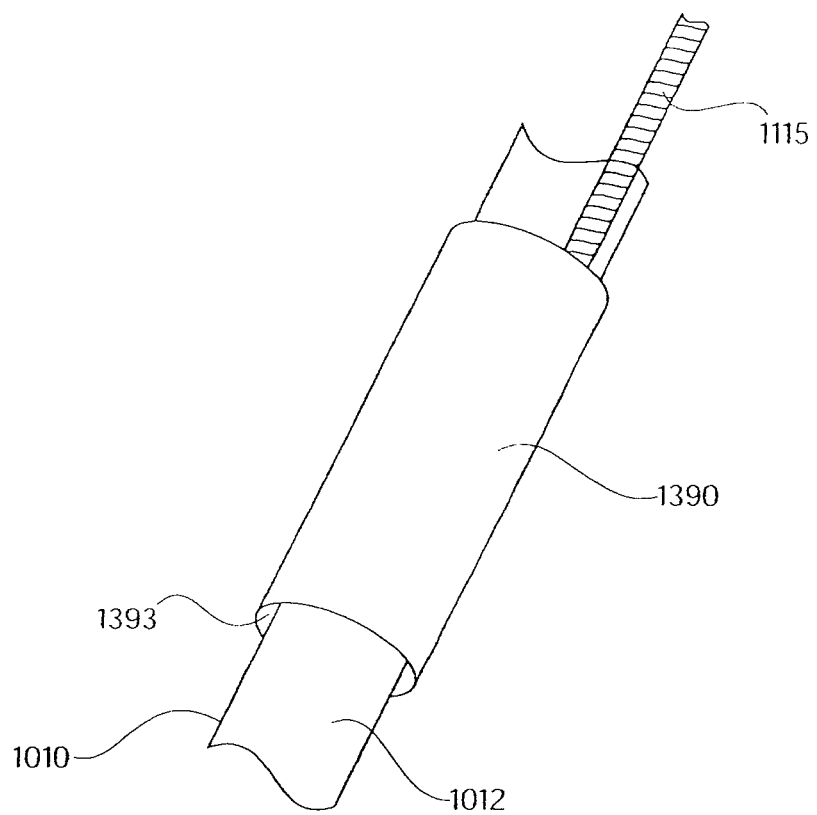
FIG. 11b is a schematic view of a portion of the trocar device illustrated in FIG. 10.

Referring now to FIGS. 11a and 11b, there is seen a more detailed view of the trocar device 1000 illustrated in FIG. 10. As illustrated in FIGS. 11a and 11b, the trocar device 1000 includes a first (e.g., rotatable) driving element 1110, connected to the first connector 18, a second (e.g., rotatable) driving element 1115 connected to the second connector 20, and a data line 1112 connected to the data connector 22. Each of the first driving element 1110, the second driving element 1115, and the data line 1112 is disposed at least partially within the housing 12. The first driving element 1110 is configured to drive the cutting blade 1120 of the cutting arrangement 1010. The second driving element 1115 is configured to extend and/or retract the cannula 1390 with respect to the cutting arrangement 1010. In one embodiment, the second driving element 1115 slidably extends and/or retracts the cannula 1390. In another embodiment, the second driving element 1115 rotatably extends and/or retracts the cannula 1390, such as described above in connection with cannula 202. In yet another example embodiment, the cannula 1390 may be extended and removed from the trocar device manually. Additionally, the cannula 1390 may include atraumatic threads as described above in connection with cannula 202.

Moreover, the trocar device 1000 may also include a memory device 1113 coupled to data line 1112. The memory device 1113 may store data relating to the operation and/or identification of the trocar device. The data may include, for example, an indication of a device type, a serial number, calibration information, usage information (e.g., an indication of a number of times the device has been utilized or, for example, an indication that the device has been utilized at all), etc. In one embodiment of the present invention, a controller in an electro-mechanical driver reads and utilizes the data stored in the memory device. The controller may, for example, choose a control program with which to control the trocar or components thereof (e.g., one or more of the driver(s)/driving element(s)) as a function of the device type. The controller may also calibrate the trocar device 1000 and/or portions of the system coupled to the trocar device, based on the calibration information. The stored serial number may be read by the controller and used for tracking, billing and inventory purposes. The controller may limit the number of times the trocar device 1000 is utilized based on data in the memory. The controller may also update information in the memory device 1113. In one embodiment, the trocar device 1000 is for single-use only. Thus, once utilized, the controller stores in the memory device 1113, an indication that the trocar device 1000 has been utilized. If an attempt is made to use the trocar device 1000 again, the controller reads the information in the memory device 1113, determines that the trocar device 1000 has already been used, and displays an error message to the operator.

The memory device 1113 may also store, for example, a control program or portion of a control program, which the controller may read and utilize to control the trocar.

It should be appreciated that the memory device 1113 may be disposed at alternate locations, such as, for example, within the cutting arrangement 1010.

It should also be appreciated that the memory device may be used with various types of trocar devices, such as, for example, a trocar with an auger and/or a trocar with a cutting blade having a generally circular profile.

Figure 12:
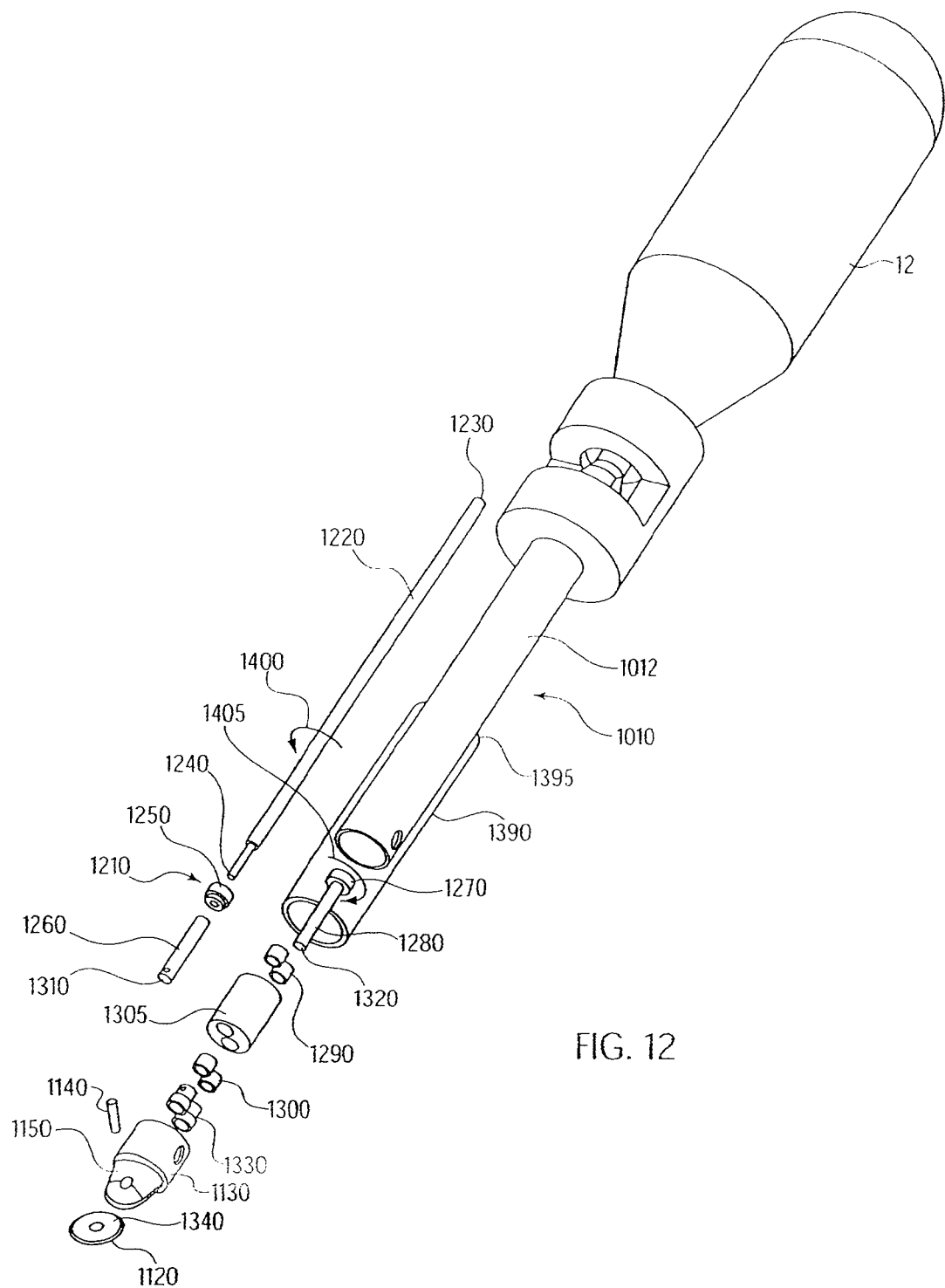
FIG. 12 is an exploded view of an exemplary trocar device according to the present invention including a dual-shaft driving arrangement.

Referring now to FIG. 12, there is seen an exploded view of the trocar device 1000 illustrated in FIG. 11 showing the first driving element 1110 having a dual-shaft driving arrangement 1210. Dual-shaft driving arrangement 1210 is at least partially disposed within the cutting arrangement 1010. Dual-shaft driving arrangement 1210 includes a main shaft 1220 having a proximal end 1230 coupled to and driven by the first connector 18 (not shown) and a distal end 1240 non-rotatably coupled to a first gear element 1250, the first gear element 1250 being non-rotatably coupled to a first drive shaft 1260.

A second gear element 1270 engages the first gear element 1250 and is non-rotatably coupled to a second drive shaft 1280. It will be appreciated that the engagement of the first gear element 1250 and the second gear element 1270 allows the second drive shaft 1280 to be rotatably driven in a second angular direction 1405 opposite to the rotation of the first drive shaft 1260 in a first angular direction 1400.

First drive shaft 1260 and second drive shaft 1280 are each received by first bearings 1290 and second bearings 1300, first bearings 1290 and second bearings 1300 being rotatably received by a securing device 1305. A distal end 1310 of first drive shaft 1260 and a distal end 1320 of second drive shaft 1280 are non-rotatably connected to respective capstans 1330, between which a proximal end 1340 of the cutting blade 1120 is frictionally engaged, the cutting blade 1120 being rotatably connected to the blade housing portion 1130 by pin 1140. Capstans 1330 may be made of any material suitable for frictionally engaging the proximal end 1340 of the cutting blade 1120, such as, for example, silicon rubber.

It should be appreciated that, although FIG. 12 illustrates the first driving element 1110 having the dual-shaft driving arrangement 1210, the present invention is intended to include other conventional driving arrangements, which may be employed to drive the cutting blade 1120 in lieu of or in addition to the dual-shaft driving arrangement 1210.

Figure 13:
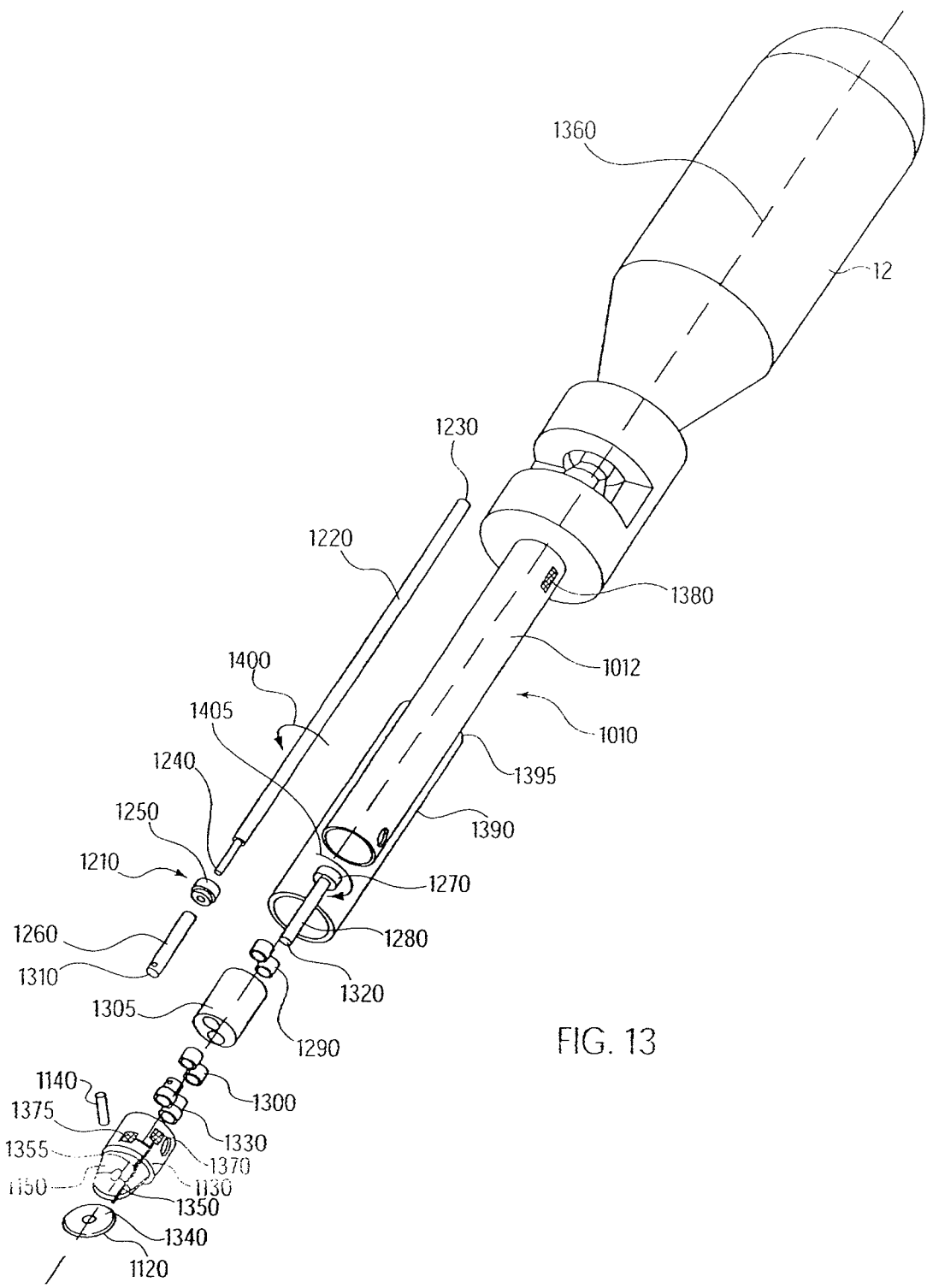
FIG. 13 is a detailed schematic view of the exemplary trocar device illustrated in FIG. 12 further including a sensing tip and a torque sensor.

Referring now to FIG. 13, there is seen a trocar device 1000 of the type illustrated in FIG. 12 further including a sensing tip 1350. The sensing tip 1350 is slidably disposed within a bore 1355 of the tapered distal end 1150 of the blade housing portion 1130 and arranged, e.g., substantially parallel to a longitudinal axis 1360 of the rotating cutter trocar device 1000. A proximal end of the sensing tip 1365 is connected to a spring element 1370, which urges the sensing tip distally with respect to the cutting blade 1120. A switch 1375 electrically and logically connected to the data line 1112 is provided for detecting proximal movement of the sensing tip 1365, as more fully set forth below.

In endoscopic surgeries, a surgeon may insufflate the abdominal cavity with $CO_2$ gas to separate the abdominal wall from the viscera. A trocar device with a $CO_2$ gas sensor may detect the presence of the $CO_2$ gas, the detection of which indicates the penetration of the trocar device into the abdominal cavity. Once the trocar device penetrates into the abdominal cavity, the electro-mechanical driver device 1 may, for example, cease operation of the cutting blade 1120.

Figure 15:
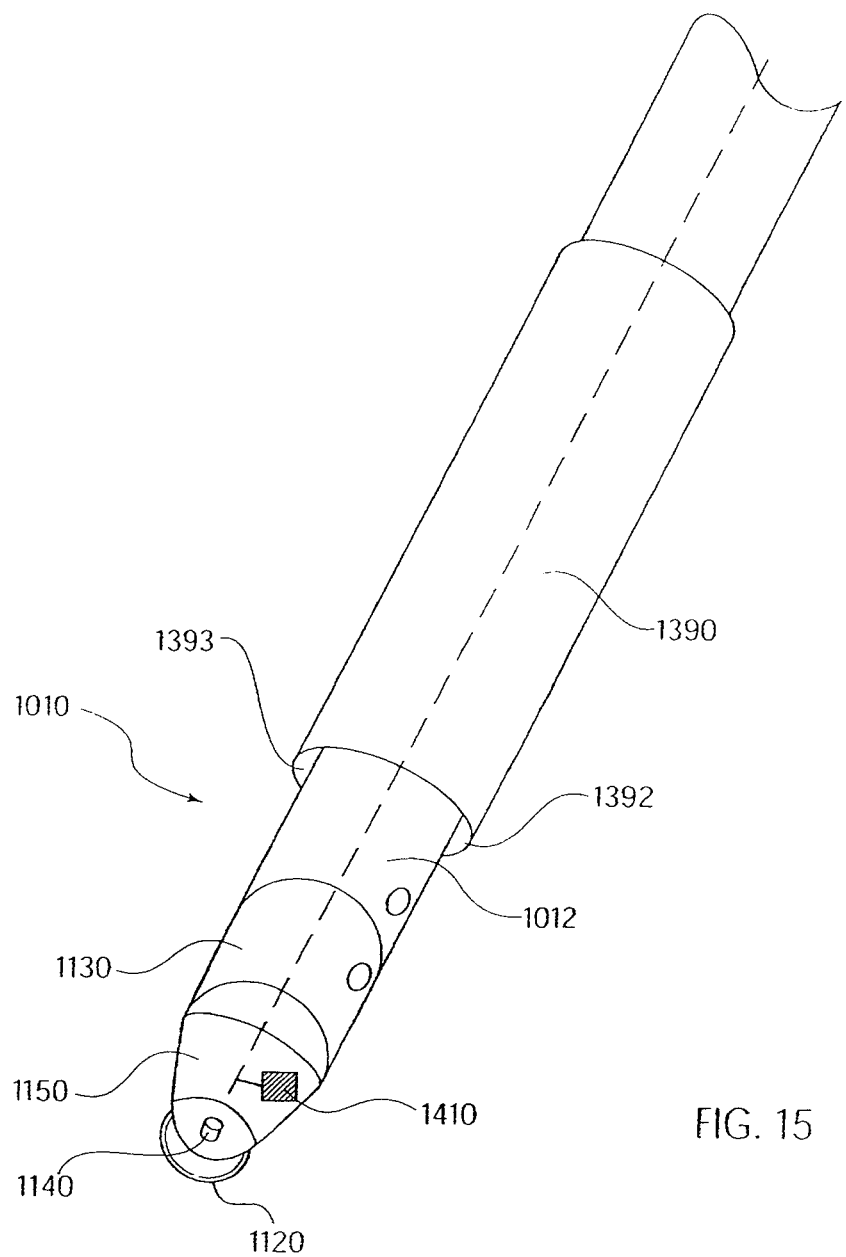
FIG. 15 is a view of a portion of an example trocar device including a gas sensor for sensing the presence of a gas.

Referring now to FIG. 15, there is seen an example embodiment of a cutting arrangement 1010 of a trocar device 1000 having a gas sensor 1410 for detecting the presence of a gas, such as, for example carbon dioxide ($CO_2$). Gas sensor 1410 may be disposed, for example, at the tapered distal end 1150 of the blade housing portion 1130 of the cutting arrangement 1010. Gas sensor 1410 is electrically connected to the data line 1112 for communicating sensed gas data to the electro-mechanical driver device 1 via the data connector 22.

It should be appreciated that the gas sensor 1410 may be disposed at alternate locations, such as, for example, within or on the blade housing portion 1130 of the cutting arrangement 1010.

It should also be appreciated that the gas sensor 1410 may be used with various types of trocar devices, such as, for example, a trocar with an auger and/or a trocar with a cutting blade having a generally circular profile.

The cutting arrangement 1010 may be provided with a torque sensor 1380 of a similar type as that described above with respect to the trocar device 200, 300. The torque sensor 1380 is electrically and logically connected to the data line 1112. In this example embodiment, the output of the torque sensor 1380 is used by the control system of the electro-mechanical driver device 1 to control the operation of the trocar device 1000, as more fully described below.

Figure 14A:
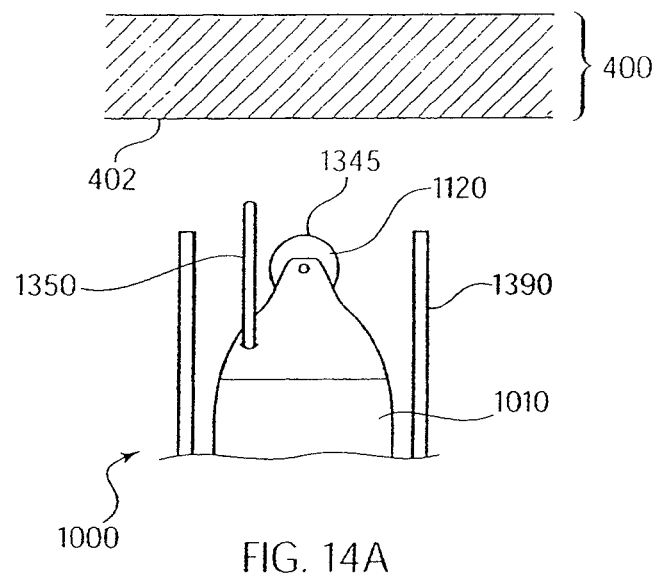
FIGS. 14A to 14E illustrate an operation sequence of the rotating-cutter trocar device illustrated in FIGS. 10 through 13.

Referring now to FIGS. 14A to 14H, there is seen on example operational sequence of the trocar device 1000 illustrated in FIGS. 10-13. FIG. 14A illustrates the trocar device 1000 prior to contacting the surface 402 of tissue 400. The trocar device 1000 or portions thereof may be sterilized some time prior to use. As illustrated in FIG. 14A, the cannula 1390 is extended beyond the cutting arrangement 1010. At least a portion of the sensing tip 1350 is arranged to extend beyond the distal end 1392 of the cannula 1390. A distal end 1345 of the cutting blade 1120 of the rotating cutter arrangement 1010 may also be configured to extend beyond the distal end 1392 of the cannula 1390 when the trocar device 1000 is in the condition prior to contacting the surface 402 of the tissue 400 as illustrated in FIG. 14A.

Figure 14B:
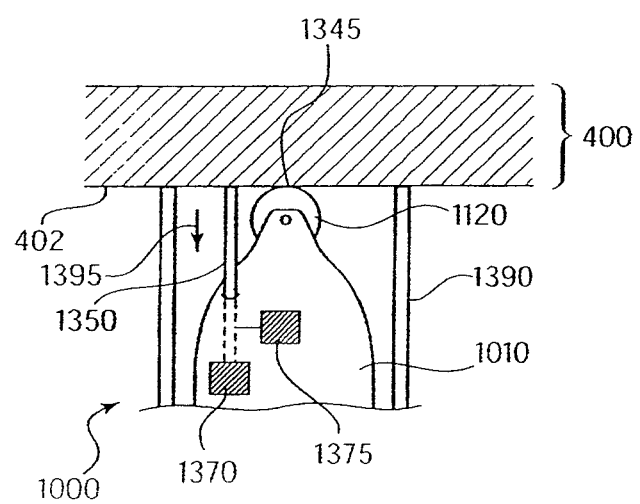

As illustrated in FIG. 14B, the trocar device 1000 is located at the intended point of incision and pressed against the surface 402 of the tissue 400. The sensing tip 1350 is caused to be displaced in the direction of the arrow 1395 and toward spring element 1370 by the pressing of the trocar device 1000 against the surface 402 of the tissue 400. The displacement of the sensing tip 1350 causes the state of the switch 1375 to change from ON to OFF or vice versa depending on whether switch 1375 is configured as a normally-closed or normally-open switch. The change of state of the switch 1375 signals the control system of the electro-mechanical driver device 1 that the trocar device 1000 is in position against the surface 402 of the tissue 400. Until the control system determines that the trocar device 1000 is in position against the surface 402 of tissue 400, in accordance with the state of switch 1375, the control system prevents the operation of the first driving element 1110 and the second driving element 1115 (not shown). In addition, the control system does not activate the first driving element 1110 and the second driving element 1115 until the appropriate control element 34, 36 of RCU 30 has been activated by the operator. Thus, in this example embodiment of the present invention, the first driving element 1110 and the second driving element 1115 are not activated until the trocar device 1000 is in position and the appropriate control element 34, 36 has been activated.

After the trocar device 1000 is placed in position against the surface 402 of tissue 400 and the operator has activated the appropriate control element 34, 36, the control system of the electro-mechanical driver device 1 activates the first driving element 1110 to rotate the cutting blade 1120.

In the case of an exemplary embodiment having the dual-shaft driving arrangement 1210 as illustrated in FIGS. 12 and 13, the electro-mechanical driver device 1 drives the first connector 18, which, in turn, rotationally drives the main shaft 1220, the first drive shaft 1260, and the first gear element 1250 in a first angular direction 1400. The rotation of first gear element 1250 causes engaged second gear element 1270 to rotate in an opposite second angular direction 1405, which, in turn, also causes second drive shaft 1260 to rotate in the second angular direction 1405 (i.e., first drive shaft 1260 and second drive shaft 1280 rotate in opposite directions). The counter-rotation of the first drive shaft 1260 and second drive shaft 1280 cause the cutting blade 1120 to rotate via the capstans 1330, which frictionally engage the proximal end 1340 of the cutting blade 1120.

During rotation of the cutting blade 1120, the torque sensor 1380 outputs a signal to the control system of the electro-mechanical driver device 1 in accordance with the torque required to continue the rotation of the cutting blade 1120. It should be appreciated that the cutting blade 1120 is configured to cut into the tissue 400.

Figure 14C:
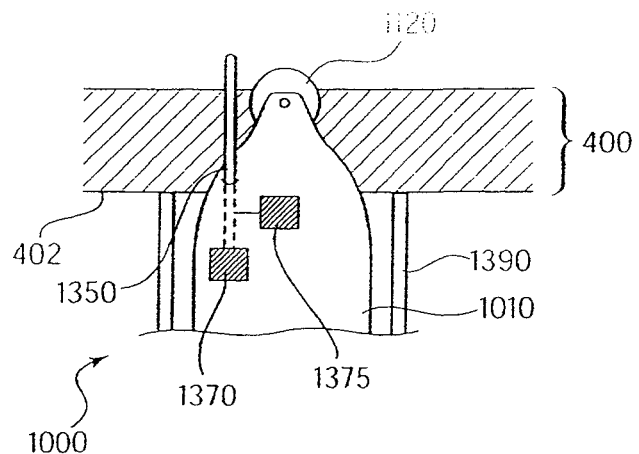
Figure 14D:
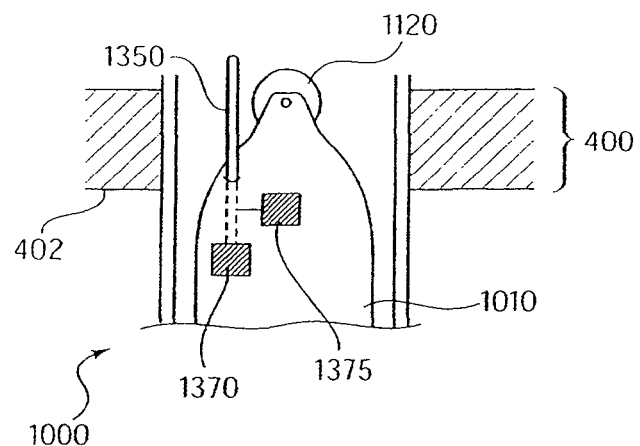
Figure 14E:
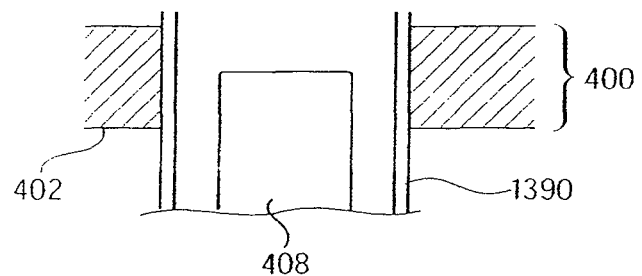

The control system of the electro-mechanical driver device 1 continues the rotation of the cutting blade 1120 until it is determined that the tapered distal end 1150 of the blade housing portion 1130 has traversed the tissue 400. This determination is made in accordance with the output of the torque sensor 1380. That is, the torque required to continue the rotation and extension of the cutting blade 1120 will decrease at the time that the tapered distal end 1150 of the blade housing portion 1130 has traversed the tissue 400. The trocar device 1000 is illustrated in FIG. 14C in the condition and position where the tapered distal end 1150 of the blade housing portion 1130 has traversed the tissue 400. In this example embodiment, in response to this condition, the control system of the electro-mechanical driver device 1 ceases rotation of the cutting blade 1120 and activates the second driving element 1115 via the second connector 20 to slide or rotate the cannula 1390, so that the cannula is displaced distally with respect to the cutting arrangement 1010, thereby drawing the cannula 1390 into the tissue 400. The cannula 1390 is drawn into the tissue 400 until the distal end 1392 of the cannula 1390 has at least traversed the tissue 400, as shown in FIG. 14D. However, it should be appreciated that the cannula 1390 may be further extended an additional length into the cavity 406. Once the control system of the electro-mechanical driver device 1 has determined that the cannula 1390 has been fully inserted into the tissue 400, the second driving element 1115 is deactivated, thereby stopping the further advancement of the cannula 1390 into the tissue 400. The cutting arrangement 1010 is subsequently withdrawn from the cannula 1390 to thereby provide access to the cavity 406 by an instrument 408 via the cannula 1390 as illustrated in FIG. 14E. It will be appreciated that a seal may be provided, for example, at the proximal end 1395 of the cannula 1390, to provide a fluid-tight and/or gas-tight seal between the cavity 406 and the environment.

After the cannula 1390 has reached its operable position, as shown in FIG. 14E, the cannula 1390 may be removed from the housing 12, to thereby provide access to the cavity 406 via the cannula 1390. Alternatively, the housing 12 may be provided with a port to provide access to the cavity 406 via the cannula 1390.

While the present invention has been particularly described, in conjunction with specific example embodiments thereof, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention. For example, in another example embodiment, the trocar may include a reciprocating cutter (and corresponding driver(s) and gears), instead of a rotating cutter.

What is claimed is:

1. A surgical device, comprising:
   a cannula defining a longitudinal axis;
   a rotatable cutter supported within the cannula and being configured to cut tissue for passage of the cannula through the tissue, the rotatable cutter including a distal edge;
   a first driver drivable by a motor arrangement and configured to rotate the rotatable cutter;
   at least one sensor assembly comprising a movable sensing tip, the movable sensing tip being offset radially from the rotatable cutter, the movable sensing tip including a distal edge and a proximal edge, the proximal edge of the movable sensing tip connects to a biasing member, the biasing member urging the movable sensing tip distally with respect to the rotatable cutter, wherein in a first position, the distal edge of the movable sensing tip extends beyond the distal edge of the rotatable cutter and wherein in a second position, the distal edge of the movable sensing tip and the distal edge of the cutter, are aligned along a plane which is perpendicular to the longitudinal axis of the surgical device, the second position being configured to signal the first driver to rotate and translate the rotatable cutter; and
   a memory device disposed in the surgical device and being configured to store data relating to at least one of, an operation of the surgical device and an identification of the surgical device, wherein the stored data is used to control an operation of the surgical device.

2. The surgical device according to claim 1, wherein the stored data includes calibration data of the surgical device, an indication of a type of surgical device, a serial number of the surgical device, an indication of usage of the surgical device, wherein the memory device is selectively connectable to a controller, and wherein the controller updates information in the memory device prior to, during and/or following use of the surgical device.

3. The surgical device according to claim 1, further comprising a controller configured to provide logical communication between the first driver and the memory device.

4. The surgical device according to claim 3, wherein the memory device is configured to store data relating to usage of the surgical device, and wherein the controller is configured to read the stored data relating to usage of the surgical device, thereby controlling the operation of the surgical device.

5. The surgical device according to claim 4, wherein the controller is configured to display an error message when the stored data indicates that the surgical device has been used.

6. The surgical device according to claim 3, wherein the memory device is configured to store at least a portion of a control program, and wherein the control program is readable by the controller to control the operation of the surgical device by the controller.

7. A method for controlling a surgical device, the method comprising:
   providing a surgical device, the surgical device including:
      a cannula defining a longitudinal axis;
      a rotatable cutter supported within the cannula and being configured to cut tissue for passage of the cannula through the tissue, the rotatable cutter including a distal edge;
      a first driver drivable by a motor arrangement and configured to rotate the rotatable cutter;
      at least one sensor assembly comprising a movable sensing tip, the movable sensing tip being offset radially from the rotatable cutter, the movable sensing tip including a distal edge and a proximal edge, the proximal edge of the movable sensing tip connects to a biasing member, the biasing member urging the movable sensing tip distally with respect to the rotatable cutter, wherein in a first position, the distal edge of the movable sensing tip extends beyond the distal edge of the rotatable cutter and wherein in a second position, the distal edge of the movable sensing tip and the distal edge of the cutter are aligned along a plane which is perpendicular to the longitudinal axis of the surgical device, the second position being configured to signal the first driver to rotate and translate the rotatable cutter; and
      a memory device disposed in the surgical device and being configured to store data relating to at least one of, an operation of the surgical device and an identification of the surgical device, wherein the stored data is used to control an operation of the surgical device;
   activating the surgical device for surgical use; and
   determining whether the surgical device has been utilized.

8. The method according to claim 7, further comprising displaying an error message to an operator if the surgical device has been previously used.

9. The method according to claim 7, further comprising providing a controller configured to provide logical communication between the first driver and the memory device.

10. The method according to claim 9, further comprising updating information stored in the memory device.

11. The method according to claim 9, further comprising storing at least a portion of a control program on the memory device, wherein the control program is readable by the controller to control the operation of the surgical device by the controller.

* * * * *